United States Patent
Cha et al.

(10) Patent No.: US 11,099,164 B2
(45) Date of Patent: Aug. 24, 2021

(54) ELECTRONIC DEVICE AND METHOD FOR UTILIZING GAS SENSOR

(71) Applicant: Samsung Electronics Co., Ltd., Suwon-si (KR)

(72) Inventors: Dohun Cha, Yongin-si (KR); Jungsik Park, Suwon-si (KR); Yongsang Yun, Osan-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 556 days.

(21) Appl. No.: 15/767,841

(22) PCT Filed: Nov. 8, 2016

(86) PCT No.: PCT/KR2016/012786
§ 371 (c)(1),
(2) Date: Apr. 12, 2018

(87) PCT Pub. No.: WO2017/082609
PCT Pub. Date: May 18, 2017

(65) Prior Publication Data
US 2018/0299417 A1  Oct. 18, 2018

(30) Foreign Application Priority Data
Nov. 11, 2015 (KR) .................. 10-2015-0158120

(51) Int. Cl.
*G01N 33/00* (2006.01)
(52) U.S. Cl.
CPC ....... *G01N 33/0031* (2013.01); *G01N 33/007* (2013.01); *G01N 33/0067* (2013.01); *H04R 2499/11* (2013.01)
(58) Field of Classification Search
CPC .......... G01N 33/0031; G01N 33/0067; G01N 33/007; H04R 2499/11
See application file for complete search history.

(56) References Cited

U.S. PATENT DOCUMENTS

| 6,182,497 B1 | 2/2001 | Krajci | |
| 6,532,801 B1 * | 3/2003 | Shan | G01M 3/22 73/170.04 |

(Continued)

FOREIGN PATENT DOCUMENTS

| CN | 1784594 A | 6/2006 |
| CN | 2935146 Y | 8/2007 |

(Continued)

OTHER PUBLICATIONS

Chen et al., "Distributed Fault Detection of Wireless Sensor Networks", DIWANS'06, Sep. 25, 2006, Los Angeles, California, USA. Copyright 2006 ACM (Year: 2006).*

(Continued)

*Primary Examiner* — Regis J Betsch
(74) *Attorney, Agent, or Firm* — Jefferson IP Law, LLP

(57) ABSTRACT

An electronic device according to various embodiments of the present invention comprises: a housing; a user interface; a first gas sensor disposed to sense gas outside the housing; a second gas sensor disposed to sense gas outside the housing and spaced apart from the first gas sensor, the second gas sensor being of the same type as the first gas sensor; a processor electrically connected to the use interface, the first gas sensor, and the second gas sensor; and a memory electrically connected to the processor, wherein the memory may store instructions, that when executed, cause the processor to: monitor the gas outside the housing using the first gas sensor to acquire first data; monitor the gas outside the housing using the second gas sensor to acquire second data; compare the first data and the second data; and provide, via the user interface, information associated with at least one of the gas, the first gas sensor and the second gas sensor, at least in part, on the basis of the comparison result. Other embodiments are also possible.

15 Claims, 19 Drawing Sheets

(56) References Cited

U.S. PATENT DOCUMENTS

| | | | |
|---|---|---|---|
| 7,049,952 B2* | 5/2006 | Kulesz | G08B 21/12 340/506 |
| 8,930,341 B2* | 1/2015 | Amin | G01N 33/0031 707/706 |
| 9,482,591 B2* | 11/2016 | Rella | G01M 3/20 |
| 2004/0066313 A1* | 4/2004 | Ong | G08C 19/04 340/870.11 |
| 2004/0173006 A1 | 9/2004 | McCoy et al. | |
| 2004/0181346 A1 | 9/2004 | Sunshine et al. | |
| 2008/0168826 A1 | 7/2008 | Saidi et al. | |
| 2011/0063116 A1* | 3/2011 | Lepley | G01N 33/0075 340/605 |
| 2011/0316699 A1* | 12/2011 | Arunachalam | G08B 29/24 340/540 |
| 2012/0013472 A1 | 1/2012 | Taylor | |
| 2014/0174153 A1* | 6/2014 | Bonisch | G01N 21/538 73/31.01 |
| 2014/0244198 A1 | 8/2014 | Mayer | |
| 2015/0298903 A1 | 10/2015 | Luxford | |
| 2015/0301004 A1 | 10/2015 | Carney et al. | |

FOREIGN PATENT DOCUMENTS

| | | |
|---|---|---|
| CN | 103109311 A | 5/2013 |
| CN | 204614170 U | 9/2015 |
| DE | 40 01 959 A1 | 7/1991 |
| EP | 194 762 A4 | 8/2002 |
| EP | 1 064 530 A4 | 12/2004 |
| EP | 2 762 877 A1 | 8/2014 |
| GB | 2 259 572 A | 3/1993 |
| KR | 10-1997-0007343 A | 2/1997 |
| KR | 10-2004-0028164 A | 4/2004 |
| KR | 10-2014-0081726 A | 7/2014 |
| KR | 10-2015-0079697 A | 7/2015 |
| WO | 2014/098691 A1 | 6/2014 |

OTHER PUBLICATIONS

Extended European Search Report dated Jul. 2, 2018, issued in the European Application No. 16864535.6.
European Office Action dated Jan. 2, 2019, issued in the European Application No. 16 864 535.6.
Chinese Office Action dated Jul. 3, 2020, issued in Chinese Application No. 201680066074.2.

* cited by examiner

ELECTRONIC DEVICE AND METHOD FOR UTILIZING GAS SENSOR

TECHNICAL FIELD

The present embodiment relates to an electronic device and, for example, to an electronic device including at least one gas sensor.

BACKGROUND ART

A variety of gases are used in industrial factories with the growth of industry, and such gases are also used for various purposes in home. Among such gases, there are flammable gases that are potentially explosive and toxic/asphyxiant gases that are poisonous to persons. If these gases are exposed to persons, life-threatening events may occur. Therefore, it is necessary to detect the leakage of dangerous gases by using a gas sensor capable of detecting various gases.

There are various types of gas sensors for detecting such gases, and typically a gas sensor using semiconductor are used in view of advantages such as sensitivity, response speed, stability, and cost. Such a semiconductor gas sensor is widely used for environmental monitoring.

Recently, the gas sensor is utilized for user health measurement by detecting the gas generated from the user. For example, such a gas sensor may be also used for detecting toxic gas such as hydrogen sulfide or sensing a user's bad breath.

DISCLOSURE OF INVENTION

Technical Problem

Measured values of the gas sensor may be varied depending on the ambient environment. When any contaminant adheres to the gas sensor, the measured values may cause a malfunction having different values from those caused by an actually occurring gas.

In addition, even if the gas sensor is equipped in a portable terminal, this typical gas sensor merely informs whether the gas is detected, and there is no way to detect a leakage direction of the gas.

Various embodiments of the present invention may improve the accuracy of gas measurement values by using a plurality of gas sensors, and provide the user with detected malfunctions of gas sensors due to contaminants adhered to the gas sensors. It is an object of various embodiments of the present invention to provide an electronic device capable of identifying a gas detected direction and a method for utilizing a gas sensor of the electronic device.

Solution to Problem

An electronic device according to various embodiments of the present invention may comprise a housing; a user interface; a first gas sensor disposed to sense a gas outside the housing; a second gas sensor disposed to sense the gas outside the housing, spaced apart from the first gas sensor, and having a same type as the first gas sensor; a processor electrically connected to the user interface, the first gas sensor, and the second gas sensor; and a memory electrically connected to the processor, wherein the memory stores instructions that cause, upon execution, the processor to acquire a first data while monitoring the gas outside the housing by using the first gas sensor, to acquire a second data while monitoring the gas outside the housing by using the second gas sensor, to compare the first data and the second data, and to provide information related to at least one of the gas, the first gas sensor, or the second gas sensor through the user interface, based on at least a part of comparison results.

A gas sensor utilization method according to various embodiments of the present invention may comprise acquiring a first data while monitoring a gas outside an electronic device by using a first gas sensor; acquiring a second data while monitoring the gas outside the electronic device by using a second gas sensor spaced apart from the first gas sensor and having a same type as the first gas sensor; comparing the first data and the second data; and providing information related to at least one of the gas, the first gas sensor, or the second gas sensor through a user interface, based on at least a part of comparison results.

Advantageous Effects of Invention

According to various embodiments of the present invention described above, it is possible to improve the accuracy of gas measurement values by using a plurality of gas sensors, and to provide the user with detected malfunctions of gas sensors due to contaminants adhered to the gas sensors. Also, it is possible to provide an electronic device capable of identifying a gas detected direction and a method for utilizing a gas sensor of the electronic device.

MODE FOR THE INVENTION

Figure 1:
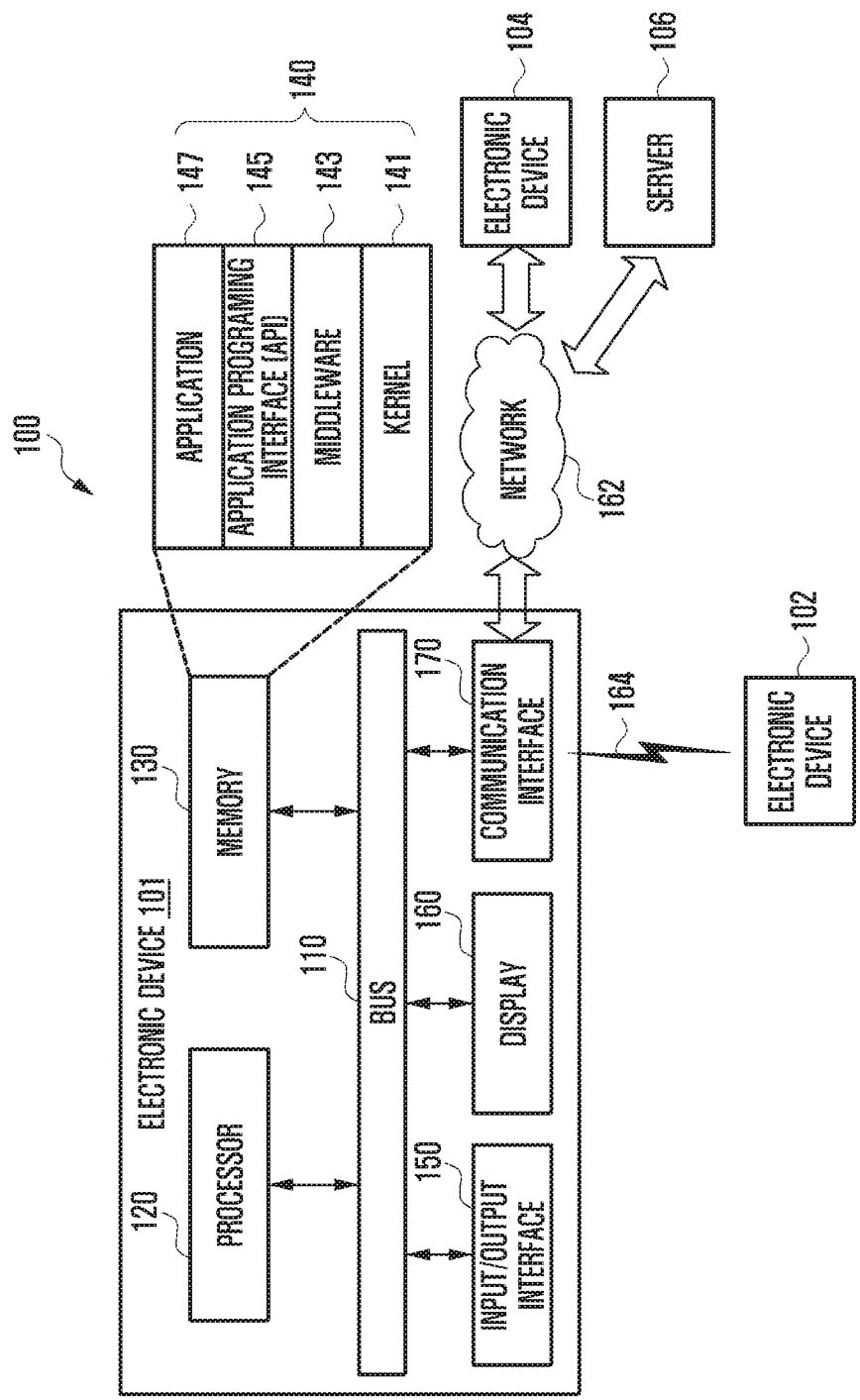
FIG. 1 illustrates an electronic device in a network environment according to various embodiments.

Hereinafter, various embodiments of the present disclosure are described with reference to the accompanying drawings. It should be understood that embodiments and terminology used therein are not intended to limit the disclosed technique to particular implementation, but various modifications, equivalents, and/or alternatives of the embodiments are included. In the description of the drawings, like reference numerals may be used for similar elements.

In this disclosure, the terms such as "comprise", "include", and "have" denote the presence of stated elements, components, operations, functions, features, and the like, but do not exclude the presence of or a possibility of addition of one or more other elements, components, operations, functions, features, and the like.

In this disclosure, the expressions "A or B", "at least one of A and/or B", and the like may include all possible combinations of items listed together. For example, "A or B", "at least one of A and B", or "at least one of A or B" may indicate all of (1) including at least one A, (2) including at least one B, and 3) including both of at least one A and at least one B.

The expressions including ordinal numbers, such as "first" and "second," may indicate various elements. The above expressions do not limit the sequence or importance of the elements, and are used merely for the purpose to distinguish one element from the others. For example, a first electronic device and a second electronic device may indicate different electronic devices regardless of the sequence or importance thereof. For example, without departing from the scope of the present disclosure, a first element may be referred to as a second element, and similarly a second element may be also referred to as a first element.

When a certain element (e.g., first element) is referred to as being "connected" or "coupled" (operatively or communicatively) to another element (e.g., second element), it may mean that the first element is connected or coupled directly to the second element or indirectly through any other element (e.g., third element). On the other hand, when a certain element (e.g., first element) is referred to as being "directly connected" or "directly coupled" to another element (e.g., second element), it may be understood that there is no element (e.g., third element) therebetween.

The expression "configured to" may be interchangeably used with any other expressions "suitable for", "having the ability to", "designed to", "adapted to", "made to", "being able to", and "capable of". The expression "device configured to" may mean that the device, together with other devices or components, "is able to". For example, the phrase "processor configured to perform A, B and C" may mean a dedicated processor (e.g., embedded processor) for performing corresponding operations or a generic-purpose processor (e.g., central processing unit (CPU) or application processor (AP)) capable of performing corresponding operations by executing one or more software programs stored in a memory.

Terms used herein may be merely to describe a certain embodiment, and may not be intended to limit the scope of other embodiments. The singular expressions may include plural expressions unless the context clearly dictates otherwise. Terms used herein, including technical or scientific terms, may have the same meaning as commonly understood by those skilled in the art. Some terms defined in a normal dictionary may be interpreted as having the same or similar meaning as the contextual meanings in the related art. Certain terms are not to be construed as an ideal or overly formal sense unless expressly defined to the contrary herein. In some cases, the terms defined herein cannot be construed to exclude embodiments of the present disclosure.

In this disclosure, an electronic device may include at least one of a smart phone, a tablet PC, a mobile phone, a video phone, an e-book reader, a desktop PC, a laptop PC, a netbook computer, a workstation, a server, a personal digital assistant (PDA), a portable multimedia player (PMP), an MP3 player, a portable medical device, a digital camera, or a wearable device. This wearable device may include at least one of an accessory-type device (e.g., a watch, a ring, a bracelet, an anklet, a necklace, glasses, a contact lens, or a head-mounted device (HMD), a fabric- or cloth-type device (e.g., electronic cloth), a body-attached type device (e.g., a skin pad or tattoo), or a body-implemented type circuit.

In some embodiments, an electronic device may include at least one of a TV, a digital video disk (DVD) player, audio equipment, a refrigerator, an air conditioner, a vacuum cleaner, an oven, a microwave, a washing machine, an air cleaner, a set-top box, a home automation control panel, a security control panel, a media box (e.g., Samsung HomeSync™, Apple TV™, or Google TV™), a game console (e.g., Xbox™, PlayStation™), an electronic dictionary, an electronic key, a camcorder, or an electronic picture frame.

In some embodiments, an electronic device may include at least one of a medical device (e.g., portable medical measuring equipment (e.g., a blood sugar meter, a heart rate meter, a blood pressure meter, a clinical thermometer, etc.), a magnetic resonance angiography (MRA), a magnetic resonance imaging (MRI), a computed tomography (CT), an ultrasonography, etc.), a navigation device, a global navigation satellite system (GNSS), an event data recorder (EDR), a flight data recorder (FDR), a car infotainment device, electronic equipment for ship (e.g., a marine navigation system, a gyrocompass, etc.), avionics, security equipment, a car head unit, an industrial or home robot, a drone, an automated teller machine (ATM), a point of sales (POS), or a device for internet of things (IoT) (e.g., a bulb, a sensor, a sprinkler, a fire alarm, a thermostat, a streetlight, a toaster, athletic equipment, a hot-water tank, a heater, a boiler, etc.).

According to some embodiments, an electronic device may be include at least one of furniture, a part of a building/construction or car, an electronic board, an electronic signature receiving device, a projector, or various measuring instruments (e.g., a water meter, an electric meter, a gas meter, a wave meter, etc.). An electronic device disclosed herein may be one of the above-mentioned devices or any combination thereof. As well understood by those skilled in the art, the above-mentioned electronic devices are exemplary only and not to be considered as a limitation of this disclosure.

Now, an electronic device according to various embodiments of the present disclosure will be described with reference to the accompanying drawings. The term user may refer to a person using the electronic device, or a device (e.g., an artificial intelligence device) using the electronic device.

Referring to FIG. 1, illustrated is an electronic device 101 in a network environment 100 according to various embodiments. The electronic device 101 may include a bus 110, a processor 120, a memory 130, an input/output (I/O) interface 150, a display 160, and a communication interface 170. In a certain embodiment, the electronic device 101 may omit at least one of the above elements or further include any other element.

The bus 110 may be a circuit which interconnects the above elements 120 to 170 and delivers a communication (e.g., a control message and/or data) between the above elements.

The processor 120 may include at least one of a central processing unit (CPU), an application processor (AP), or a communication processor (CP). The processor 120 may execute an operation or data processing for control and/or communication of at least one of other elements.

The memory 130 may include volatile and/or non-volatile memory. The memory 130 may store instructions or data related to at least one element of the electronic device 101. According to an embodiment, the memory 130 may store software and/or programs 140. The programs 140 may include, for example, a kernel 141, a middleware 143, an application programming interface (API) 145, and/or an application program (or application) 147. At least some of the kernel 141, the middleware 143, and the API 145 may be referred to as an operating system (OS).

The kernel 141 may control or manage system resources (e.g., the bus 110, the processor 120, the memory 130, etc.) used to execute operations or functions implemented in other programs (e.g., the middleware 143, the API 145, and the application program 147). Also, the kernel 141 may provide an interface capable of accessing individual elements of the electronic device 101 through the middleware 143, the API 145, or the application program 147, and thereby controlling or managing system resources.

The middleware 143 may perform a function of an intermediary so that the API 145 or the application program 147 communicates with the kernel 143 and thereby exchanges data.

In addition, the middleware 143 may process one or more work requests, received from the application program 147, according to priorities. For example, the middleware 143 may assign, to the application program 147, a priority for using system resources (e.g., the bus 110, the processor 120, the memory 130, etc.) of the electronic device 101 and then process the one or more work requests.

The API 145 is an interface through which the application 147 controls a function provided by the kernel 141 or the middleware 143, and may include, for example, at least one interface or function (e.g., instructions) for file control, window control, image processing, character control, and/or the like.

The I/O interface 150 may transmit commands or data, inputted from a user or other external device, to other element(s) of the electronic device 101, or output commands or data, received from other element(s) of the electronic device 101, to a user or other external device.

The display 160 may include, for example, a liquid crystal display (LCD), a light-emitting diode (LED) display, an organic light-emitting diode (OLED) display, a micro-electro-mechanical systems (MEMS) display, or an electronic paper display. The display 160 may display, for example, various contents (e.g., text, image, video, icon, symbol, etc.) to a user. The display 160 may include a touch screen and may receive, for example, a touch, gesture, proximity, or hovering input using an electronic pen or a portion of the user's body.

The communication interface 170 may establish communication between the electronic device 101 and an external device (e.g., a first external electronic device 102, a second external electronic device 104, or a server 106). For example, the communication interface 170 may be connected to the network 162 via wireless or wired communication and communicate with an external device (e.g., the second external electronic device 104 or the server 106).

The wireless communication may include cellular communication using at least one of, for example, LTE, LTE Advance (LTE-A), code division multiple access (CDMA), wideband CDMA (WCDMA), universal mobile telecommunications system (UMTS), wireless broadband (WiBro), global system for mobile communications (GSM), and the like. According to an embodiment, the wireless communication may include at least one of, for example, wireless fidelity (WiFi), Bluetooth, Bluetooth low power (BLE), Zigbee, near field communication (NFC), magnetic secure transmission, radio frequency (RF), or body area network (BAN). According to an embodiment, the wireless communication may include GNSS. The GNSS may be, for example, global positioning system (GPS), global navigation satellite system (Glonass), Beidou navigation satellite system (Beidou), or Galileo, the European global satellite-based navigation system. Hereinafter, in this disclosure, "GPS" may be used interchangeably with "GNSS". The wired communications may include at least one of, for example, a universal serial bus (USB), a high definition multimedia interface (HDMI), a recommended standard 232 (RS-232), a power line communication, or a plain old telephone service (POTS). The network 162 may include a telecommunications network, for example, at least one of a computer network (e.g., LAN or WAN), the Internet, or a telephone network.

Each of the first and second external electronic devices 102 and 104 may be similar to or different from the electronic device 101 in types. According to various embodiments, all or part of operations performed in the electronic device 101 may be performed in another electronic device or multiple electronic devices (e.g., the electronic devices 102 and 104 and the server 106). According to an embodiment, in case of having to perform a certain function or service automatically or on demand, the electronic device 101 may request any other electronic device (e.g., the electronic device 102 or 104 or the server 106) to perform at least part of the function or service rather than or in addition to autonomously performing the function or service. Then, the other electronic device (e.g., the electronic device 102 or 104 or the server 106) may perform the requested function or service and return a result to the electronic device 101. The electronic device 101 may provide the requested function or service by using or further processing the received result. For this, cloud computing technique, distributed computing technique, or client-server computing technique may be utilized for example.

Figure 2:
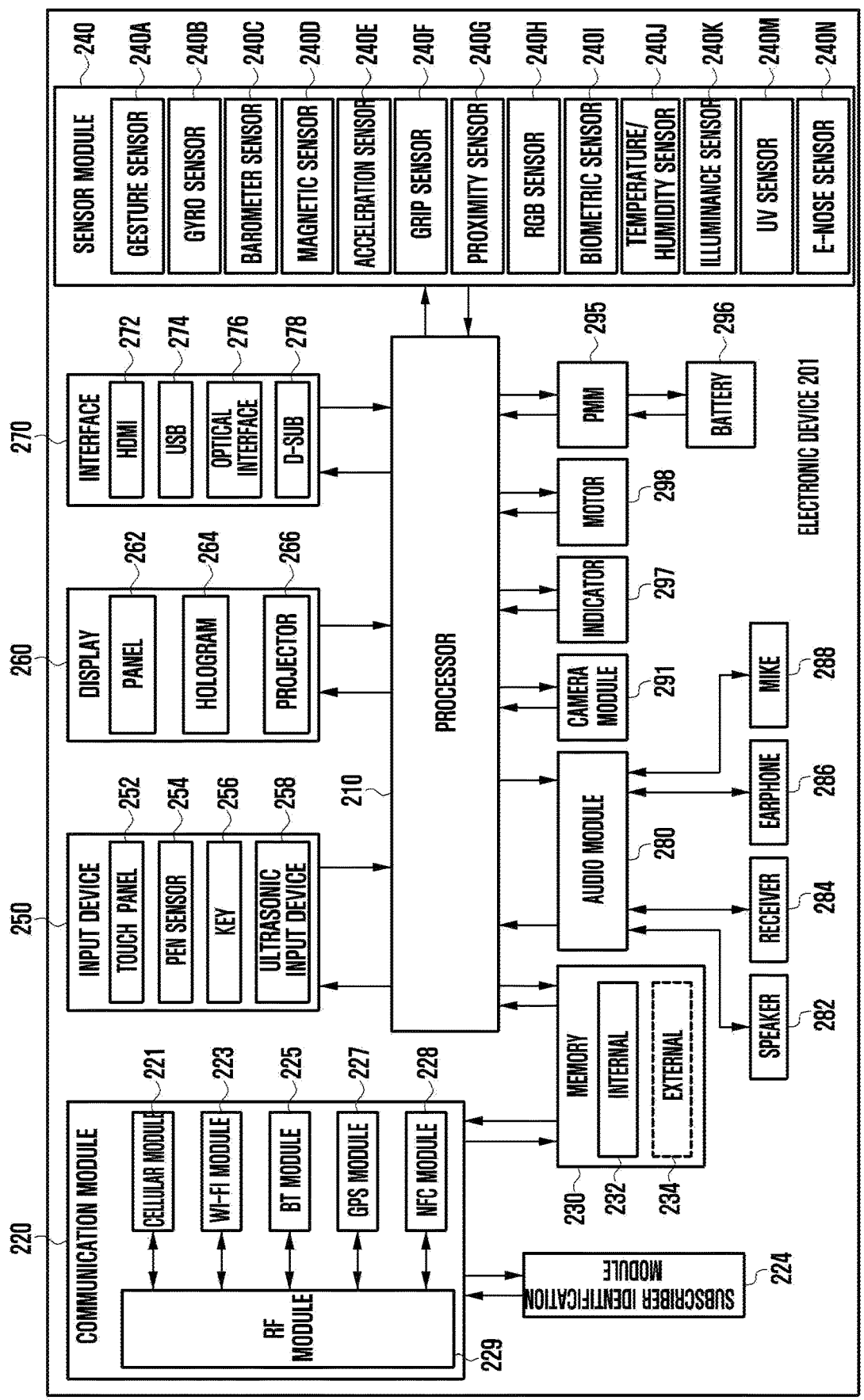
FIG. 2 is a block diagram illustrating an electronic device according to various embodiments.

FIG. 2 is a block diagram illustrating an electronic device 201 according to embodiments. The electronic device 201 may form, for example, the whole or part of the electronic device 101 shown in FIG. 1. The electronic device 201 may include at least one application processor (AP) 210, a communication module 220, a subscriber identification module (SIM) card 224, a memory 230, a sensor module 240, an input device 250, a display 260, an interface 270, an audio module 280, a camera module 291, a power management module 295, a battery 296, an indicator 297, and a motor 298.

The processor 210 may execute an operating system (OS) or an application program, control multiple hardware or software components connected to the processor 210, and perform processing and operations on various data. The processor 210 may be implemented by, for example, a system on chip (SoC). According to an embodiment, the processor 210 may further include a graphic processing unit (GPU) and/or an image signal processor. The processor 210 may include at least some of elements shown in FIG. 2 (e.g., a cellular module 221). The processor 210 may load and process instructions or data received from at least one of the other elements (e.g., non-volatile memory) into volatile memory and then store the resulting data in non-volatile memory.

The communication module 220 may be, for example, the communication module 170 shown in FIG. 1. The communication module 220 may include, for example, a cellular module 221, a Wi-Fi module 223, a Bluetooth (BT) module 225, a GNSS module 227 (e.g., a GPS module, a Glonass module, a Beidou module, or a Galileo module), an NFC module 228, and a radio frequency (RF) module 229.

The cellular module 221 may provide a voice call, a video call, a messaging service, or an Internet service, for example, through a communication network. According to an embodiment, the cellular module 221 may utilize the subscriber identity module (e.g., a SIM card) 224 to perform the identification and authentication of the electronic device 201 in the communication network. According to an embodiment, the cellular module 221 may perform at least some of functions that the processor 210 may provide. According to an embodiment, the cellular module 221 may include a communications processor (CP).

Each of the WiFi module 223, the Bluetooth module 225, the GNSS module 227, and the NFC module 228 may include a processor for processing data transmitted or received therethrough. According to a certain embodiment, at least some (e.g., two or more) of the cellular module 221, the WiFi module 223, the Bluetooth module 225, the GNSS module 227, or the NFC module 228 may be included in an integrated chip (IC) or an IC package.

The RF module 229 may, for example, transmit and receive communication signals (e.g., RF signals). The RF module 229 may include, for example, a transceiver, a power amplifier module (PAM), a frequency filter, a low noise amplifier (LNA), or an antenna. According to another embodiment, at least one of the cellular module 221, the WiFi module 223, the Bluetooth module 225, the GNSS module 227, or the NFC module 228 may transmit and receive RF signals through separate RF modules.

The SIM 224 may include, for example, a card having SIM or an embedded SIM, and may include unique identification information (e.g., an integrated circuit card identifier (ICCID), or an international mobile subscriber identity (IMSI)).

The memory 230 (e.g., the memory 130 shown in FIG. 1) may include an internal memory 232 and an external memory 234. The internal memory 232 may include, for example, at least one of a volatile memory (e.g., a DRAM, an SRAM, or SDRAM), and a non-volatile memory (e.g., a one time programmable ROM (OTPROM), a PROM, an EPROM, an EEPROM, a mask ROM, a flash ROM, a flash memory, a hard drive, or a solid state drive (SSD)).

The external memory 234 may include a flash drive, for example, a compact flash (CF), a secure digital (SD), a micro-SD, a mini-SD, an extreme Digital (xD), or a memory stick. The external memory 234 may be functionally or physically connected to the electronic device 201 through various interfaces.

The sensor module 240 may, for example, measure a physical quantity or sense an operating state of the electronic device 201 and convert the measured or sensed information into an electrical signal. The sensor module 240 may include, for example, at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., RGB (red, green and blue) sensor), a biometric sensor 240I, a temperature/humidity sensor 240J, an illuminance sensor 240K, a ultra violet (UV) sensor 240M, or an e-nose sensor 240N. The e-nose sensor 240N is a sensor capable of sensing various kinds of gases such as $CO_2$, CO, $O_2$, and $NO_2$, and may be formed of a semiconductor sensor. The E-nose sensor may be implemented as a chip including a separate device for sensing each gas. In case of being in contact with a corresponding gas, each device may be changed in electrical properties (e.g., dielectric constant, resistance, impedance, etc.) and output an altered electric signal (e.g., voltage or current). Additionally or alternatively, the sensor module 240 may include, for example, an electromyography (EMG) sensor, an electroencephalogram (EEG) sensor, an electroardiogram (ECG) sensor, an infrared (IR) sensor, an iris sensor, and/or a fingerprint sensor. The sensor module 240 may further include a control circuit for controlling one or more sensors included therein. In a certain embodiment, the electronic device 201 further includes a processor configured to control the sensor module 240, either as part of the processor 210 or separately, to control the sensor module 240 while the processor 210 is in a sleep state.

The input device 250 may include various input circuitry, such as, for example, and without limitation, a touch panel 252, a digital pen sensor 254, a key 256, or an ultrasonic input unit 258. The touch panel 252 may recognize a touch input in a manner of capacitive type, resistive type, infrared type, or ultrasonic type. Also, the touch panel 252 may further include a control circuit. In case of a capacitive type, a physical contact or proximity may be recognized. The touch panel 252 may further include a tactile layer. In this case, the touch panel 252 may offer a tactile feedback to a user.

The digital pen sensor 254 may be formed in the same or similar manner as receiving a touch input or by using a separate recognition sheet. The key 256 may include, for example, a physical button, an optical key, or a keypad. The ultrasonic input unit 258 is a specific device capable of identifying data by sensing sound waves with a microphone 288 through an input tool that generates ultrasonic signals, thus allowing wireless recognition.

The display 260 (e.g., the display 160) may include a panel 262, a hologram 264, or a projector 266. The panel 262 may be, for example, LCD (Liquid Crystal Display), AM-OLED (Active Matrix Organic Light Emitting Diode), or the like. The panel 262 may have a flexible, transparent or wearable form. The panel 262 may be formed of a single module with the touch panel 252. The hologram 264 may show a stereoscopic image in the air using interference of light. The projector 266 may project an image onto a screen, which may be located at the inside or outside of the electronic device 201. According to an embodiment, the display 260 may further include a control circuit for controlling the panel 262, the hologram 264, and the projector 266.

The interface 270 may include various interface circuitry, such as, for example, and without limitation, an HDMI (High-Definition Multimedia Interface) 272, a USB (Universal Serial Bus) 274, an optical interface 276, or a D-sub (D-subminiature) 278. The interface 270 may be contained, for example, in the communication interface 170 shown in FIG. 1. Additionally or alternatively, the interface 270 may include, for example, an MHL (Mobile High-definition Link) interface, an SD (Secure Digital) card/MMC (Multi-Media Card) interface, or an IrDA (Infrared Data Association) interface.

The audio module 280 may perform a conversion between sounds and electric signals. The audio module 280 may process sound information inputted or outputted through a speaker 282, a receiver 284, an earphone 286, or a microphone 288.

The camera module 291 is a device capable of acquiring still images and moving images. According to an embodiment, the camera module 291 may include at least one image sensor (e.g., a front sensor or a rear sensor), a lens (not shown), an ISP (Image Signal Processor, not shown), or a flash (e.g., LED or xenon lamp, not shown).

The power management module 295 may manage electric power of the electronic device 201. Although not shown, the power management module 295 may include, for example, a PMIC (Power Management Integrated Circuit), a charger IC, or a battery or fuel gauge. The PMIC may be formed, for example, of an IC chip or SoC. Charging may be performed in a wired or wireless manner. The charger IC may charge a battery 296 and prevent overvoltage or overcurrent from a charger. According to an embodiment, the charger IC may have a charger IC used for at least one of wired and wireless charging types. A wireless charging type may include, for example, a magnetic resonance type, a magnetic induction type, or an electromagnetic type. Any additional circuit for a wireless charging may be further used such as a coil loop, a resonance circuit, or a rectifier. The battery gauge may measure the residual amount of the battery 296 and a voltage, current or temperature in a charging process. The battery 296 may store or create electric power therein and supply electric power to the electronic device 201. The battery 296 may be, for example, a rechargeable battery or a solar battery.

The indicator 297 may show thereon a current status (e.g., a booting status, a message status, or a recharging status) of the electronic device 201 or of its part (e.g., the AP 210). The motor 298 may convert an electric signal into a mechanical vibration. Although not shown, the electronic device 201 may include a specific processor (e.g., GPU) for supporting a mobile TV. This processor may process media data that comply with standards of DMB (Digital Multimedia Broadcasting), DVB (Digital Video Broadcasting), or media flow.

Each of the above-discussed elements of the electronic device disclosed herein may be formed of one or more components, and its name may be varied according to the type of the electronic device. The electronic device disclosed herein may be formed of at least one of the above-discussed elements without some elements or with additional other elements. Some of the elements may be integrated into a single entity that still performs the same functions as those of such elements before integrated.

Figure 3:
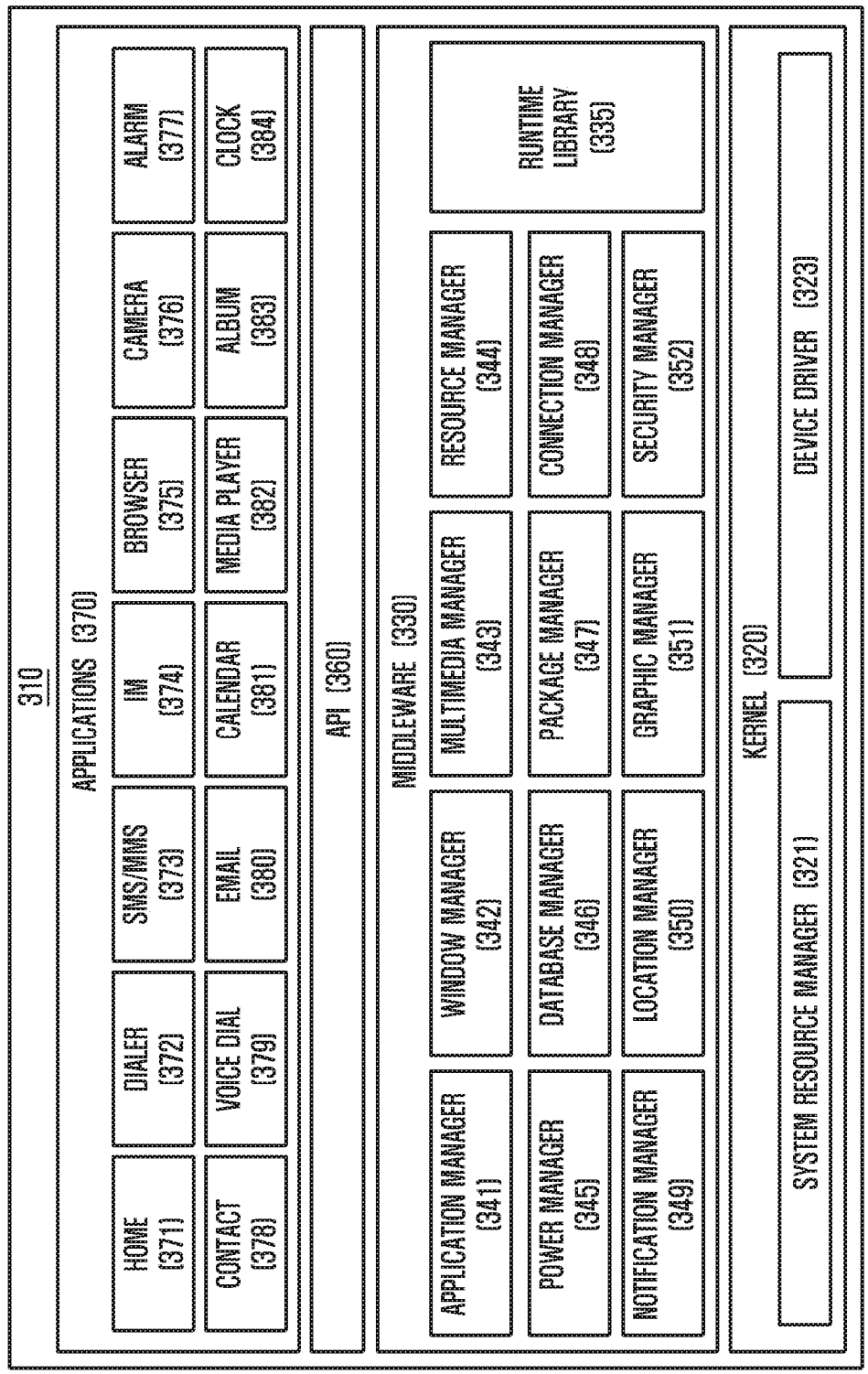
FIG. 3 is a block diagram illustrating a program module according to various embodiments.

FIG. 3 is a block diagram illustrating a program module according to various embodiments. According to one embodiment, the program module 310 (e.g., the program 140) may include an OS controlling resources related to an electronic device (e.g., the electronic device 101) and/or various applications (e.g., the application program 147) executed in the OS. For example, the OS may be Android, iOS, Windows, Symbian, Tizen, Bada, and the like.

The program module 310 may include a kernel 320, a middleware 330, an API 360, and/or the application 370. At least a part of the program module 310 may be preloaded in the electronic device or downloaded from an external electronic device (e.g., the electronic device 102, 104 or the server 106).

The kernel 320 (e.g., the kernel 141) may include a system resource manager 321 and/or a device driver 323. The system resource manager 321 may perform the control, allocation, recovery, and/or the like of system resources. According to one embodiment, the system resource manager 321 may include a process manager, a memory manager, or a file system manager. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver.

The middleware 330 may include multiple modules previously implemented so as to provide a function used in common by the applications 370. Also, the middleware 330 may provide a function to the applications 370 through the API 360 in order to enable the applications 370 to efficiently use limited system resources within the electronic device. For example, as illustrated in FIG. 3, the middleware 330 (e.g., the middleware 143) may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, a security manager 352, and any other suitable and/or similar manager.

The runtime library 335 may include, for example, a library module used by a complier, in order to add a new function by using a programming language during the execution of the application 370. According to an embodiment of the present disclosure, the runtime library 335 may perform functions which are related to input and output, the management of a memory, an arithmetic function, and/or the like.

The application manager 341 may manage, for example, a life cycle of at least one of the applications 370. The window manager 342 may manage GUI resources used on the screen. For example, when at least two displays 260 are connected, the screen may be differently configured or managed in response to the ratio of the screen or the action of the application 370. The multimedia manager 343 may detect a format used to reproduce various media files and may encode or decode a media file through a codec appropriate for the relevant format. The resource manager 344 may manage resources, such as a source code, a memory, a storage space, and/or the like of at least one of the applications 370.

The power manager 345 may operate together with a Basic Input/Output System (BIOS), may manage a battery or power, and may provide power information and the like used for an operation. The database manager 346 may manage a database in such a manner as to enable the generation, search and/or change of the database to be used by at least one of the applications 370. The package manager 347 may manage the installation and/or update of an application distributed in the form of a package file.

The connectivity manager 348 may manage a wireless connectivity such as, for example, Wi-Fi and Bluetooth. The notification manager 349 may display or report, to the user, an event such as an arrival message, an appointment, a proximity alarm, and the like in such a manner as not to disturb the user. The location manager 350 may manage location information of the electronic device. The graphic manager 351 may manage a graphic effect, which is to be provided to the user, and/or a user interface related to the graphic effect. The security manager 352 may provide various security functions used for system security, user authentication, and the like. According to an embodiment, when the electronic device (e.g., the electronic device 101) has a telephone function, the middleware 330 may further include a telephony manager for managing a voice telephony call function and/or a video telephony call function of the electronic device.

The middleware 330 may include a middleware module for forming various functional combinations of the above-described elements. The middleware 330 may provide modules specialized according to types of OSs in order to provide differentiated functions. Also, the middleware 330 may dynamically delete some of the existing elements, or may add new elements.

The API 360 (e.g., the API 145) is a set of API programming functions, and may be provided with a different configuration according to an OS. In the case of Android or iOS, for example, one API set may be provided to each platform. In the case of Tizen, for example, two or more API sets may be provided to each platform.

The applications 370 (e.g., the applications 147) may include, for example, a home application 371, a dialer application 372, a Short Message Service (SMS)/Multimedia Message Service (MIMS) application 373, an Instant Message (IM) application 374, a browser application 375, a camera application 376, an alarm application 377, a contact application 378, a voice dial application 379, an electronic mail (e-mail) application 380, a calendar application 381, a media player application 382, an album application 383, a clock application 384, or at least one application capable of performing functions such as health care (e.g., measurement of exercise amount or blood glucose) or environmental information provision (e.g., providing information about air pressure, humidity, temperature, or the like).

According to one embodiment, the applications 370 may include an application (hereinafter, referred to as "information exchange application") that supports the exchange of information between the electronic device (e.g., 101) and an external electronic device (e.g., 102 or 104). The information exchange application may include, for example, a notification relay application for delivering specific information to the external electronic device, or a device management application for managing the external electronic device.

For example, the notification relay application may have a function of sending notification information generated in other applications (e.g., the SMS/MMS application, the email application, the healthcare application, or the environmental information application) of the electronic device to the external electronic device (e.g., 102 or 104). Further, the notification relay application may receive notification information from the external electronic device and provide it to the user.

The device management application may manage (e.g., install, delete, or update) at least one function (e.g., turn-on/turn-off of the external electronic device itself or some components thereof or adjusting the brightness or resolution of the display) of the external electronic device (e.g., 102 or 104), at least one application running in the external electronic device, or at least one service (e.g., a call service or a message service) provided in the external electronic device.

According to one embodiment, the applications 370 may include an application (e.g., a healthcare application of a mobile medical device, etc.) designated depending on the attributes of the external electronic device (e.g., 102 or 104). According to one embodiment, the applications 370 may include an application received from the external electronic device (e.g., the server 106 or the electronic device 102 or 104). According to one embodiment, the applications 370 may include a preloaded application or a third party application downloadable from a server. The names of elements of the program module 310 according to the illustrated embodiment may be varied depending on the type of the operating system.

According to various embodiments, at least a part of the program module 310 may be implemented in software, firmware, hardware, or a combination thereof. At least a part of the program module 310 may be implemented (e.g., executed) by, for example, a processor (e.g., 210). At least a part of the program module 310 may include, for example, modules, programs, routines, sets of instructions, or processes to perform one or more functions.

The term "module" used in this disclosure may mean a unit including, for example, one or a combination of hardware, software, and firmware. The term "module" may be interchangeably used with other terms, for example, such as unit, logic, logical block, component, or circuit. The "module" may be the minimum unit, or a part thereof, of an integrally constructed component. The "module" may be the minimum unit, or a part thereof, for performing one or more functions. The "module" may be implemented mechanically or electronically. For example, according to the present disclosure, the "module" may include at least one of an application-specific integrated circuit (ASIC) chip, field-programmable gate arrays (FPGAs), and a programmable-logic device, which are known or to be developed later and perform particular functions.

According to various embodiments, at least a part of the device (e.g., modules or functions thereof) or the method (e.g., operations) may be implemented, for example, as instructions stored in a non-transitory computer-readable storage medium in a programming module form. When the instructions are executed by a processor (e.g., the processor 120), the processor may execute a function corresponding to the instructions. The computer-readable storage medium may be, for example, the memory 130.

The non-transitory computer-readable recording medium may include magnetic media such as a hard disk, a floppy disk, and a magnetic tape, optical media such as a Compact Disc Read Only Memory (CD-ROM) and a Digital Versatile Disc (DVD), magneto-optical media such as a floptical disk, and hardware devices specially configured to store and perform a program instruction. In addition, the program instructions may include high class language codes, which can be executed in a computer by using an interpreter, as well as machine codes made by a compiler. The hardware devices described above may be configured to operate as one or more software modules to perform the operations of the various embodiments, and vice versa.

A module or programming module according to various embodiments may include or exclude at least one of the above-discussed components or further include any other component. The operations performed by the module, programming module, or any other component according to various embodiments may be executed sequentially, in parallel, repeatedly, or by a heuristic method. Additionally, some operations may be executed in different orders or omitted, or any other operation may be added.

Hereinafter, an electronic device and a method for utilizing a gas sensor of the electronic device according to various embodiments of the present invention will be described in detail.

Figure 4A:
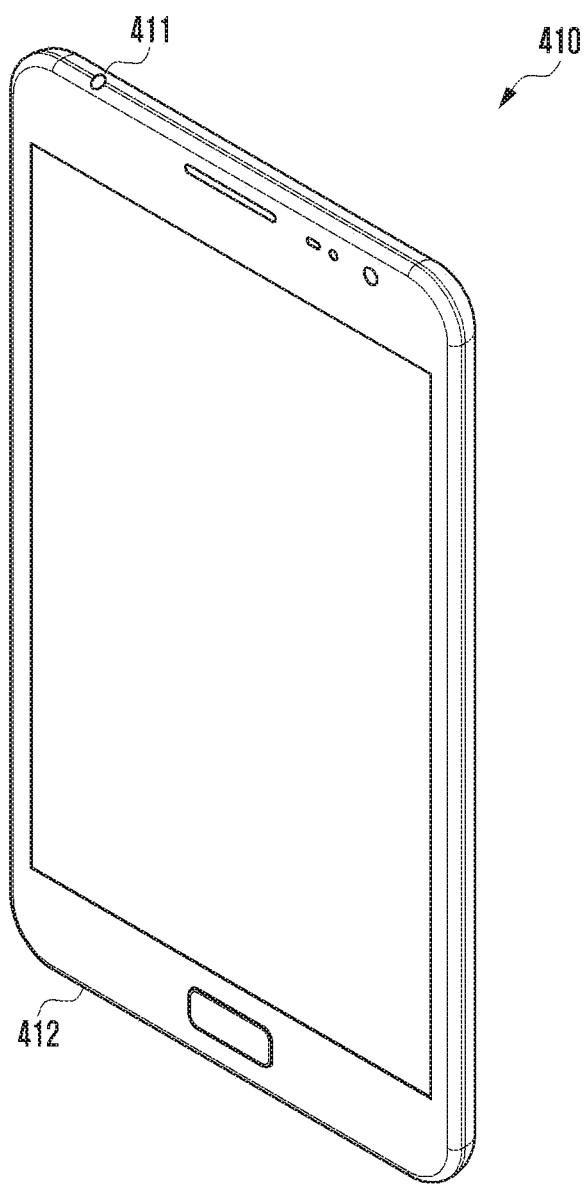
FIGS. 4A and 4B illustrate examples of an electronic device according to various embodiments of the present invention.
Figure 4B:
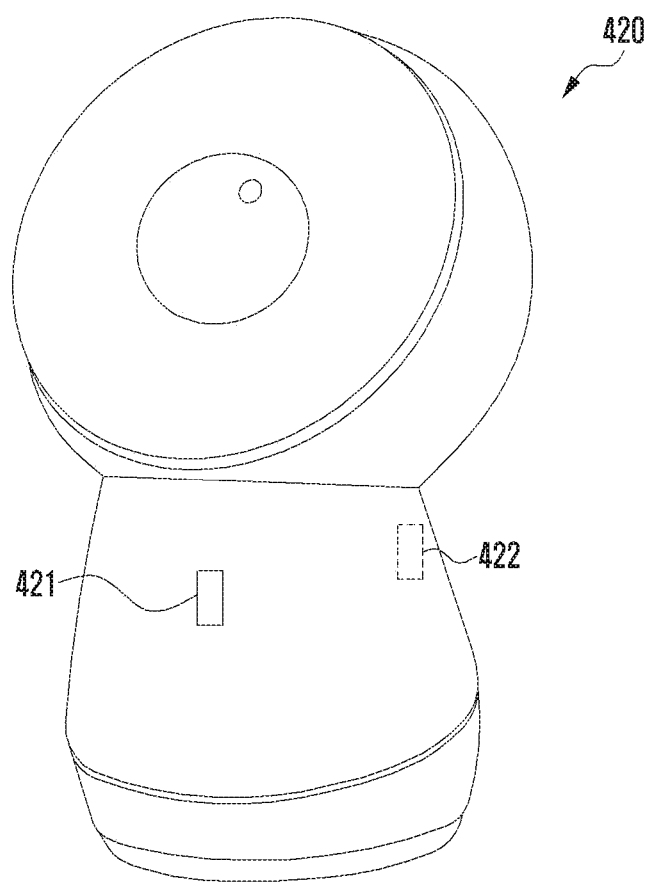

FIGS. 4A and 4B illustrate examples of an electronic device according to various embodiments of the present invention.

As shown in FIG. 4A, the electronic device 410 according to various embodiments of the present invention may be implemented as a portable terminal that can be carried by a user. For example, the electronic device 410 may be implemented as a smart phone, a tablet personal computer (tablet PC), or the like, and may operate various applications in addition to an essential telephony function.

The electronic device 410 may include at least one gas sensor, e.g., two gas sensors 411 and 412. As shown in FIG. 4A, the first gas sensor 411 may be equipped at the upper end of the electronic device 410, and the second gas sensor 412 may be equipped at the lower end of the electronic device 410. However, the first and second gas sensors 411 and 412 are not limited to the above positions and may be located in opposite directions in the electronic device 410. Each of the first and second gas sensors 411 and 412 may be located in a hole for a microphone, a speaker, etc. typically provided in the electronic device 410.

As shown in FIG. 4B, the electronic device 420 according to various embodiments of the present invention may be implemented as a robot. An illustrated form is merely one example in various embodiments and may be implemented with, but not limited to, a variety of known domestic or industrial robots. As shown in FIG. 4B, the first gas sensor 421 may be equipped on the front surface of the electronic device 420, and the second gas sensor 422 may be equipped on the rear surface of the electronic device 420. However, the first and second gas sensors 411 and 412 are not limited to the above positions and may be located in opposite directions in the electronic device 410.

Meanwhile, the electronic devices 410 and 420 described through FIGS. 4A and 4B are merely examples in various embodiments of the present invention. According to various embodiments of the present invention, various kinds of electronic devices that include at least one gas sensor capable of measuring a gas exposed to the outside of the electronic device and also have a processor capable of processing a signal detected through the gas sensor may be provided.

Figure 5:
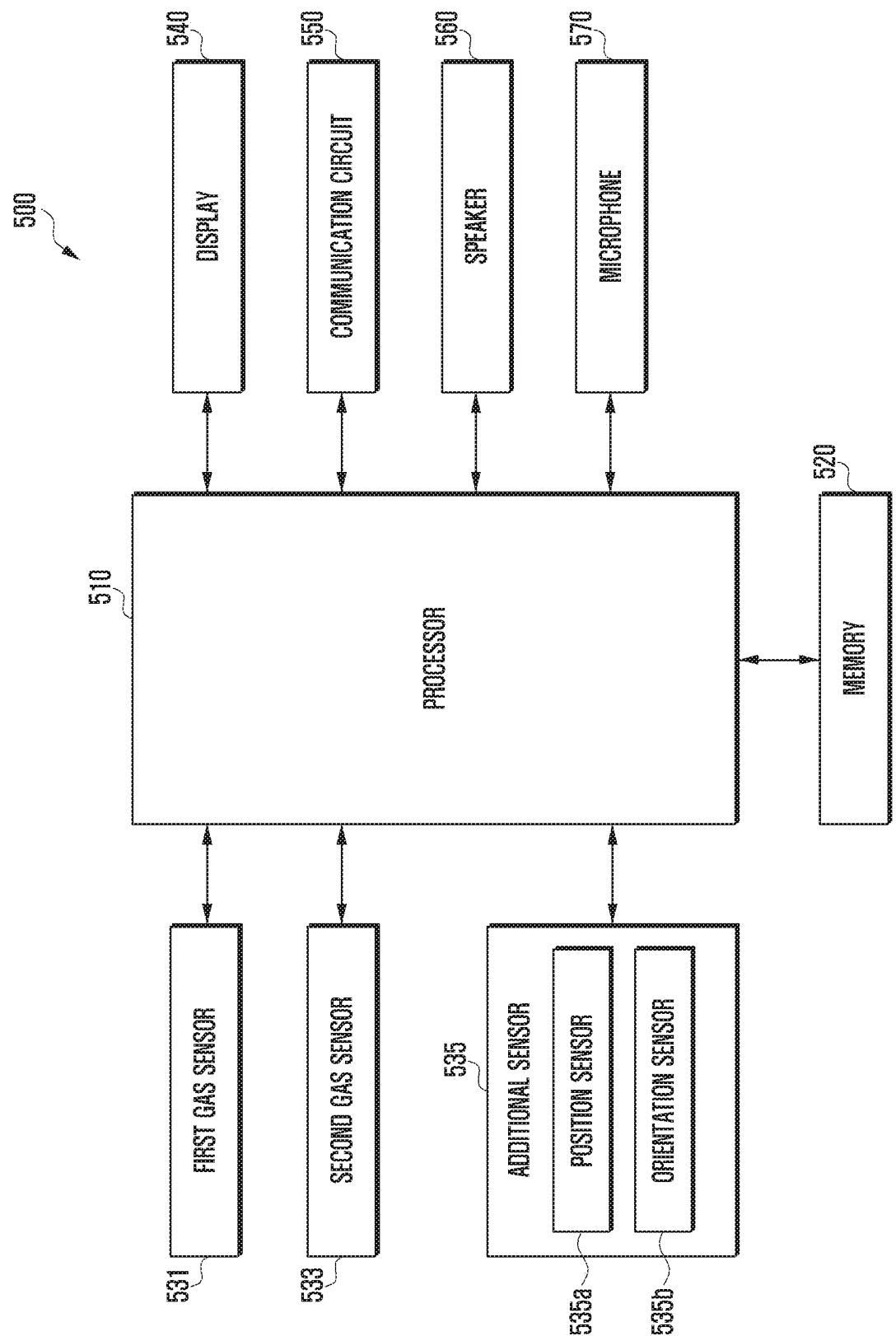
FIG. 5 is a block diagram illustrating an electronic device according to one of various embodiments of the present invention.

FIG. 5 is a block diagram illustrating an electronic device according to one of various embodiments of the present invention.

As shown, the electronic device 500 may include at least one sensor 531, 533, and 535, a processor 510, a memory 520, a display 540, a communication circuit 550, a speaker 560, and a microphone 570. The at least one sensor may include a first gas sensor 531, a second gas sensor 533, and an additional sensor 535. The additional sensor 535 may include a position sensor 535a and an orientation sensor 535b, and may also have various kinds of sensors, such as a temperature sensor and a humidity sensor, other than a gas sensor. Even if at least some of elements shown in FIG. 5 are omitted or substituted, it is possible to implement various embodiments of the present invention.

The first gas sensor 531 and the second gas sensor 533 are sensors capable of sensing various kinds of gases such as $CO_2$, CO, $O_2$, and $NO_2$, and may be formed of semiconductor sensors. Each of the first and second gas sensors 531 and 533 may be implemented as at least one chip including a separate device for sensing each gas. When being in contact with a corresponding gas, each device may be changed in electrical properties (e.g., dielectric constant, resistance, impedance) and may output an altered electric signal (e.g., voltage or current). The first and second gas sensors 531 and 533 may include at least a part of the e-nose sensor 240N earlier described in FIG. 2.

The first and second gas sensors 531 and 533 are equipped to detect a gas from the outside of the electronic device 500, and may be located in opposite directions on the housing of the electronic device 500 in order to check a gas detected direction and a malfunction thereof. For example, the first gas sensor 531 may be equipped at the upper end of the electronic device 500, and the second gas sensor 533 may be equipped at the lower end of the electronic device 500.

The first gas sensor 531 may monitor a gas outside the housing of the electronic device 500 and thereby acquire first data. The second gas sensor 533 may monitor a gas outside the housing of the electronic device 500 and thereby acquire second data. The first and second gas sensors 531 and 533 may monitor an external gas in real time in a turned-on state and, when the electrical property thereof is changed due to contact with the external gas, may output the first and second data to the processor 510 to be described below.

According to various embodiments, the first and second gas sensors 531 and 533 may be the same kind of gas sensor. That is, the first and second gas sensors 531 and 533 may be formed of the same semiconductor sensor and have the same electrical property that is changed during gas contact. Thus, the first data and the second data, which are generated respectively, may be available for sensing the same kind of gas. However, depending on the positions where the first and second gas sensors 531 and 533 are disposed in the electronic device 500, the degree and amount of a detected gas, a detected time, and the like may be varied.

According to another embodiment, the first and second gas sensors 531 and 533 may be different kinds of gas sensors. According to still another embodiment, the first and second gas sensors 531 and 533 may be a composite gas sensor capable of detecting one or more gases, and the kinds of gases that can be detected by the first and second gas sensors 531 and 533 may be the same at least partially.

Although FIG. 5 shows two gas sensors, i.e., the first gas sensor 531 and the second gas sensor 533, the electronic device 500 may alternatively have three or more gas sensors.

The additional sensor 535 may include at least one of various kinds of sensors, other than the gas sensor, that may be implemented in the electronic device 500, and may include at least some of sensors of the sensor module 240 earlier described in FIG. 2. The additional sensor 535 may include, for example, the position sensor 535a for detecting a current location of the electronic device 500, and the orientation sensor 535b for sensing the orientation of the electronic device 500. Also, the additional sensor 535 may include various kinds of sensors such as a temperature sensor and a humidity sensor.

The memory 520 may include a volatile memory and a nonvolatile memory, which are well known and not limited to specific implementation. The memory 520 stores various instructions that can be executed by the processor 510. These instructions may include control commands such as arithmetic and logic operations, data transfer, and input/output that can be recognized by the processor 510.

The display 540 is an element for displaying an image and may include at least a part of the display 160 in FIG. 1 and/or at least a part of the display 260 in FIG. 2. A panel (not shown) of the display 540 may be combined with a touch panel (not shown) of the input device to form a single module. The display 540 may output a certain image under the control of the processor 510 to be described below. According to various embodiments of the present invention, the display 540 may output a user interface related to a gas detection, a gas detected direction, and/or a malfunction of the gas sensor. In this case, the user interface may be composed of a layer different from the output image and displayed on an upper layer than the image.

The communication circuit 550 is an element for transmitting and receiving data to and from an external device (e.g., an external electronic device and/or a server device). The communication circuit 550 may include at least a part of the communication interface 170 in FIG. 1 and/or at least a part of the communication module 220 in FIG. 2.

The speaker 560 may amplify and output an audio signal under the control of the processor 510. The speaker 560 may be located in a hole formed at, but not limited to, the upper end of the electronic device 500. The first gas sensor 531 or the second gas sensor 533 may be located in this hole where the speaker 560 is equipped.

The microphone 570 may collect a user's voice or surrounding sounds from the outside. The microphone 570 may be located in a hole formed at, but not limited to, the lower end of the electronic device 500. The first gas sensor 531 or the second gas sensor 533 may be located in this hole where the microphone 570 is equipped.

A structure that the speaker 560, the microphone 570, the first gas sensor 531, and the second gas sensor 533 are disposed in holes will be described below with reference to FIG. 6.

The processor 510 is an element to perform operating or data processing on control and/or communication of the respective elements of the electronic device 500, and may include at least a part of the processor 120 in FIG. 1 and/or at least a part of the application processor 210 in FIG. 2. Although the operating and data processing functions implemented in the electronic device 500 by the processor 510 are not limited, the following description will be made with respect to functions of processing and operating signals detected from the first gas sensor 531, the second gas sensor 533, and the additional sensor 535, for example, compensating an output depending on changes in environment, checking a contamination state of the gas sensor, checking the directionality of a detected gas, and the like.

The processor 510 may be electrically connected to the respective elements of the electronic device 500 such as the first gas sensor 531, the second gas sensor 533, the additional sensor 535, the memory 520, the display 540, the communication circuit 550, the speaker 560, and the microphone 570.

When the processor 510 receives the first data from the first gas sensor 531 and the second data from the second gas sensor 533, the processor 510 may compare the first data and the second data and, based on at least a part of comparison results, provide information related to at least one of the detected gas, the first gas sensor 531, and/or the second gas sensor 533 though the user interface. The above-described functions of the processor 510 may be performed by loading the above-described instructions stored in the memory 520.

The user interface is configured to provide processing results of the processor 510 to the user and to receive a user feedback, and may be a graphical user interface (GUI) displayed on the display 540 or an audio signal outputted through the speaker 560. The user interface outputted depending on sensing results of the gas sensor in the electronic device 500 may provide information related to at least one of the detected gas, the first gas sensor 531, and/or the second gas sensor 533. Specifically, the user interface may provide information about the occurrence of a gas, a gas occurrence direction, the malfunction of the first gas sensor 531 and/or the second gas sensor 533, and the like. Examples of information that the electronic device 500 outputs through the user interface will be described below with reference to FIGS. 9A, 9B, and 11.

Figure 6:
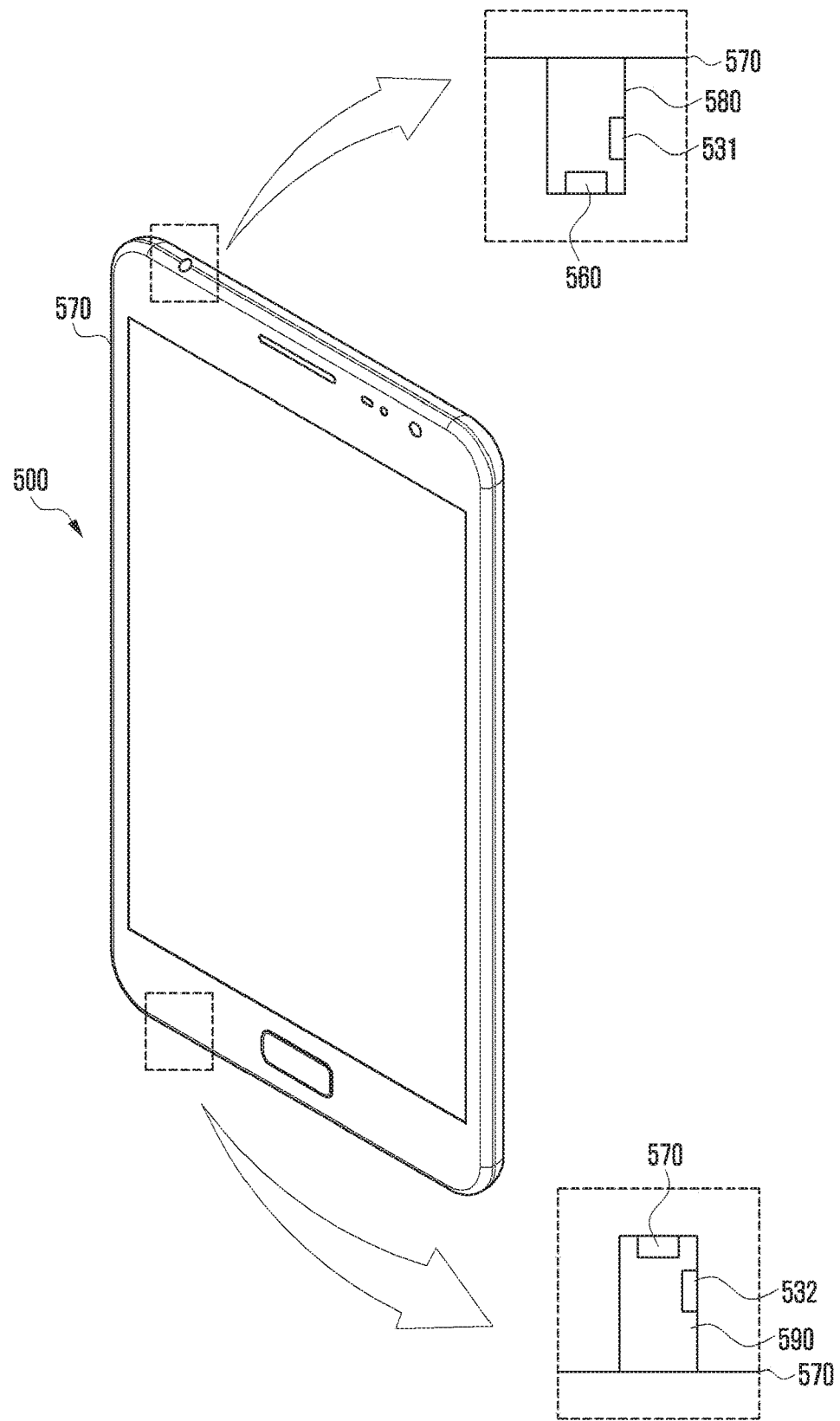
FIG. 6 illustrates an example of the arrangement of a first gas sensor and a second gas sensor according to various embodiments of the present invention.

FIG. 6 illustrates an example of the arrangement of a first gas sensor and a second gas sensor according to various embodiments of the present invention.

The electronic device 500 includes a housing 570, which may be provided with at least one space for the gas sensor to measure a gas. This space may include an opening or hole, which may contain a porous material (e.g., coretex) for waterproofing. The gas sensor may be located in each space, and the additional sensor 535 such as a humidity sensor or a temperature sensor may be located in at least one other space.

The electronic device 500 may include a first hole 580 formed in a portion of the housing 570, and a second hole 590 formed in another portion of the housing 570 and different in position from the first hole 580. The first gas sensor 531 and the second gas sensor 533 may be located within the first hole 580 and the second hole 590, respectively, to measure the gas distributed around the electronic device 500.

As shown in FIG. 6, the first hole 580 may be formed at the upper end of the electronic device 500, and the second hole 590 may be formed at the lower end of the electronic device 500. These positions are not limited to the upper and lower ends. For example, the first hole 580 and the second hole 590 may be spaced apart from each other at a certain distance to identify a gas detection direction through the respective gas sensors, and may be located in opposite directions on the housing 570 of the electronic device 500.

The first hole 580 may be bored into a first surface (e.g., the top surface) of the housing 570 in a first direction (e.g., from the upper end of the housing 570 to the lower end), and the second hole 590 may be bored into a second surface (e.g., the bottom surface) of the housing 570 in a second direction (e.g., from the lower end of the housing 570 to the upper end) opposite to the first direction.

The first gas sensor 531 may be disposed in the first hole 580, and also at least one speaker 560 may be disposed in the first hole 580 as shown. In addition, the second gas sensor 533 may be disposed in the second hole 590, and also at least one microphone 570 may be disposed in the second hole 590 as shown. That is, the at least one microphone 570 and/or the at least one speaker 560 may be configured to acquire or output a sound signal through the first hole 580 or the second hole 590.

In the electronic device 500 according to various embodiments of the present invention, the first and second gas sensors 531 and 533 are disposed in holes typically equipped for the microphone 570 or the speaker 560 without requiring separate holes for collecting the gas. Advantageously, this may eliminate unnecessary design for a separate hole arrangement.

Figure 7A:
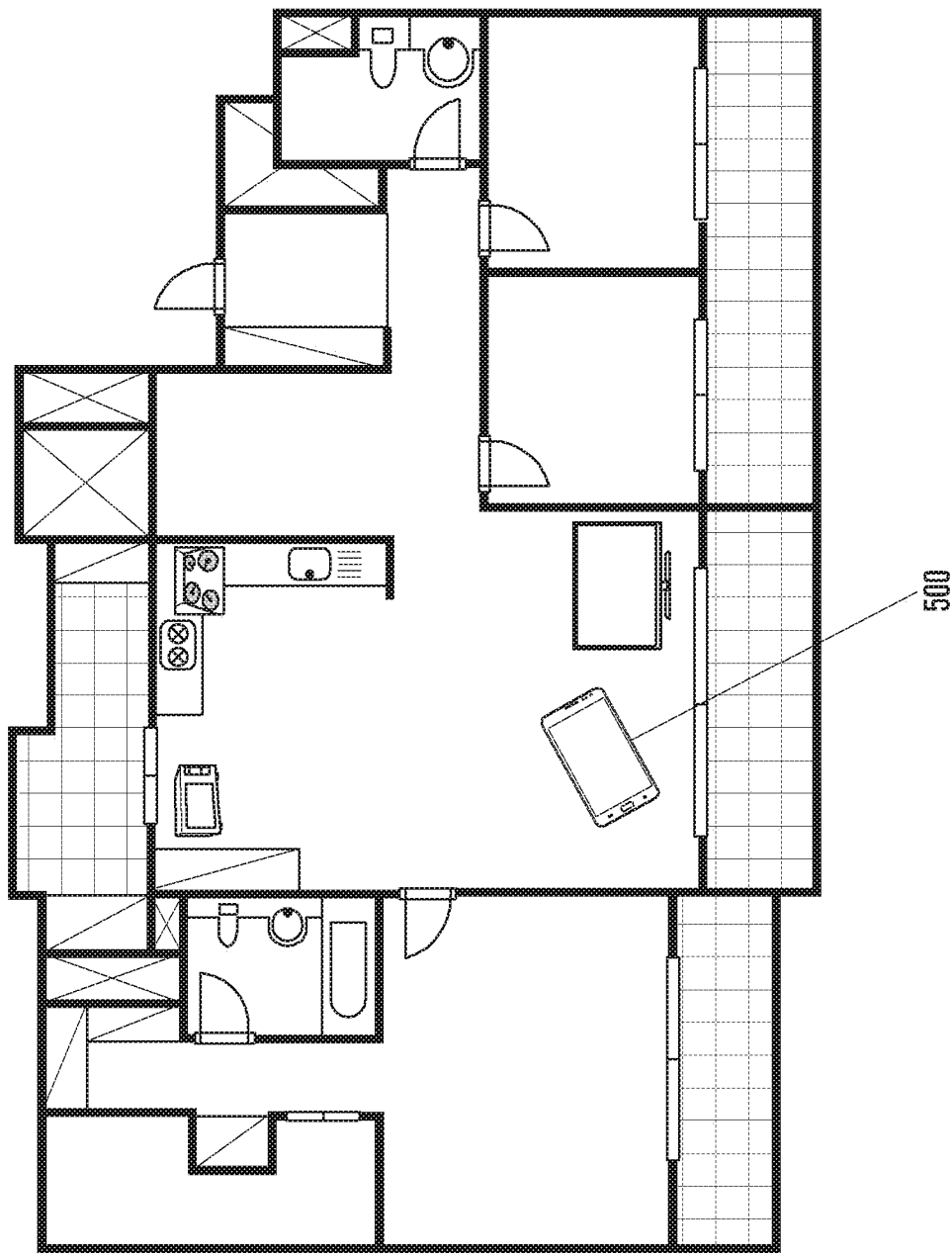
FIGS. 7A and 7B illustrate examples of utilizing an electronic device in a home environment according to various embodiments of the present invention.
Figure 7B:
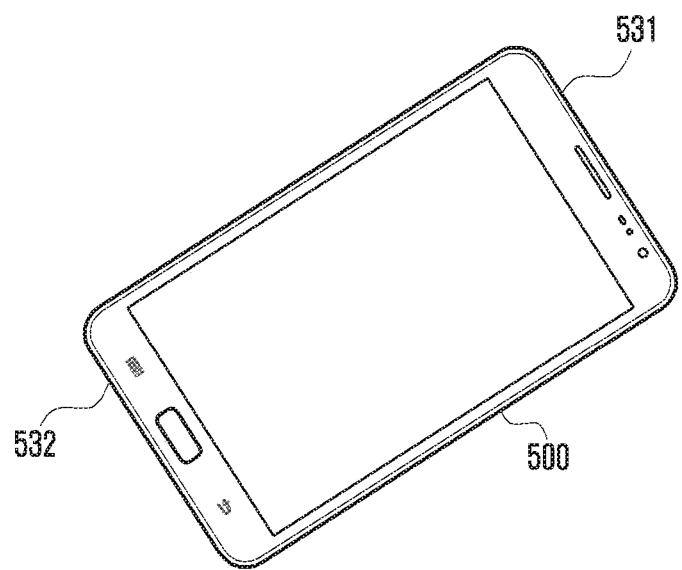

FIGS. 7A and 7B illustrate examples of utilizing an electronic device in a home environment according to various embodiments of the present invention.

As shown, the electronic device 500 may be located in home and utilized to identify a gas detection in home. As described above, the electronic device 500 may include at least one gas sensor capable of detecting gases such as $CO_2$, CO, $O_2$, $NO_2$, and the like, and may monitor an air pollution state in home through the detected gases. For example, an indoor air condition may deteriorate when cooked in a kitchen or due to household goods, furniture, and the operation of indoor electronic devices.

Using the first gas sensor 531 and the second gas sensor 533, the electronic device 500 may detect the gas occurring in home and also find a gas occurrence position. For this, the memory 520 of the electronic device 500 may store data about an indoor structure of home.

According to various embodiments, the electronic device 500 may recognize a current location thereof in a particular environment through the additional sensor 535 (e.g., the position sensor 535a and/or the orientation sensor 535b). For example, as shown in FIG. 7A, the electronic device 500 may be located in a path between a kitchen and a room. In such a case, the electronic device 500 may calculate the location thereof by receiving RF signals and using a measuring technique such as a time of arrival (TOA), a time difference of arrival (TDOA), or a received signal strength indication (RSSI). Alternatively, the electronic device 500 may calculate the location thereof by performing location tracking through IC chip identifier (TAG) or measuring ambient environments through an optical device (not shown). Further, the electronic device 500 may identify the orientation thereof through the orientation sensor (e.g., a compass sensor).

As shown in FIG. 7B, the electronic device 500 includes the first gas sensor 531 and the second gas sensor 533, which may be located in opposite directions, such as the upper and lower ends of the electronic device 500, respectively. For example, when the current orientation of the electronic device 500 is toward the kitchen at the upper end and is toward the room at the lower end as shown in FIG. 7B, the gas diffused from the kitchen is firstly detected by the first gas sensor 531 and then detected by the second gas sensor 533. Also, the gas diffused from the room may be detected by the first gas sensor 531 after being detected by the second gas sensor 533. In this case, the electronic device 500 may identify, through the orientation sensor, the orientation in which the electronic device 500 is placed, and may also identify a relative position of gas occurrence through detected values of the first and second gas sensors 531 and 533 and the orientation sensor.

Figure 8:
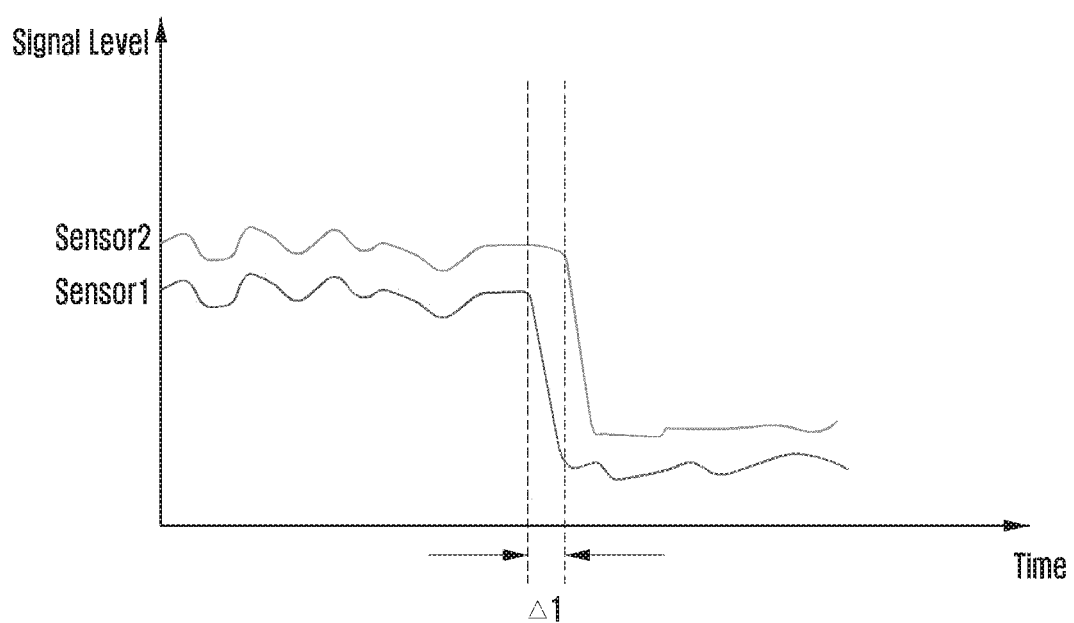
FIG. 8 is a graph showing time-varying signal levels of first data and second data according to various embodiments of the present invention.

FIG. 8 is a graph showing time-varying signal levels of first and second data detected by first and second gas sensors according to various embodiments of the present invention. FIG. 8 shows signal levels detected by the first and second gas sensors in a state of no malfunction.

As described above, the first and second gas sensors 531 and 533 may be implemented as semiconductor sensors. According to intrinsic properties of the semiconductor sensor, electrical properties (e.g., dielectric constant, resistance, impedance, etc.) of the first and second gas sensors 531 and 533 may be changed when the gas is detected, and thereby the level of output signals may be lowered. When the output signal level is lowered, the first and second gas sensors 531 and 533 output the first and second data, respectively, to the processor 510. The first data and the second data may include a signal level and time information.

Even though no gas occurs outside the electronic device 500, the output signal level of the gas sensor may be fluid within a certain range due to the ambient environment. In this case, if the fluidly varying output signal level is large, there is a possibility of wrongly determining that the gas is detected. In the electronic device 500 including the first and second gas sensors 531 and 533 according to various embodiments of the present invention, the output signals of the first and second gas sensors 531 and 533 may have varying values of a similar level when fluidity is caused by the ambient environment. Thus, both signals may be regarded as being fluctuated due to a change in the environment, and may indicate a specific signal ratio (e.g., a difference between first and second data levels being smaller than a reference value).

If the gas occurs outside the electronic device 500, the output level of the gas sensor may be lowered to a large extent as shown. In this case, the electronic device 500 may estimate a detected direction of the gas by using a varying time point of the output signal of the first and second data.

The processor 510 may calculate a difference between a first time point of detecting the gas by the first gas sensor 531 and a second time point of detecting the gas by the second gas sensor 533. Then, based on the calculated difference in time, the processor 510 may determine the occurrence direction of the gas. Referring to FIG. 8, the output signals of the first and second gas sensors 531 and 533 are maintained at a similar level. Then, the output level of the first gas sensor 531 is reduced first, and the output level of the second gas sensor 533 is reduced after an elapse of a certain time ($\Delta 1$). In this case where the first gas sensor 531 earlier detects the gas occurrence than the second gas sensor 533, the electronic device 500 may estimate that the gas occurs in a direction where the first gas sensor 531 is located.

As described above, the electronic device 500 may identify an indoor location thereof by using the additional sensor 535 (e.g., the position sensor 535a and the orientation sensor 535b), and store data about an indoor structure of home in the memory 520. Therefore, when finding the direction of gas occurrence as described above, the electronic device 500 may acquire information about a specific indoor place (e.g., a kitchen or a room) located in the gas occurrence direction by utilizing the stored data about the indoor structure.

Figure 9A:
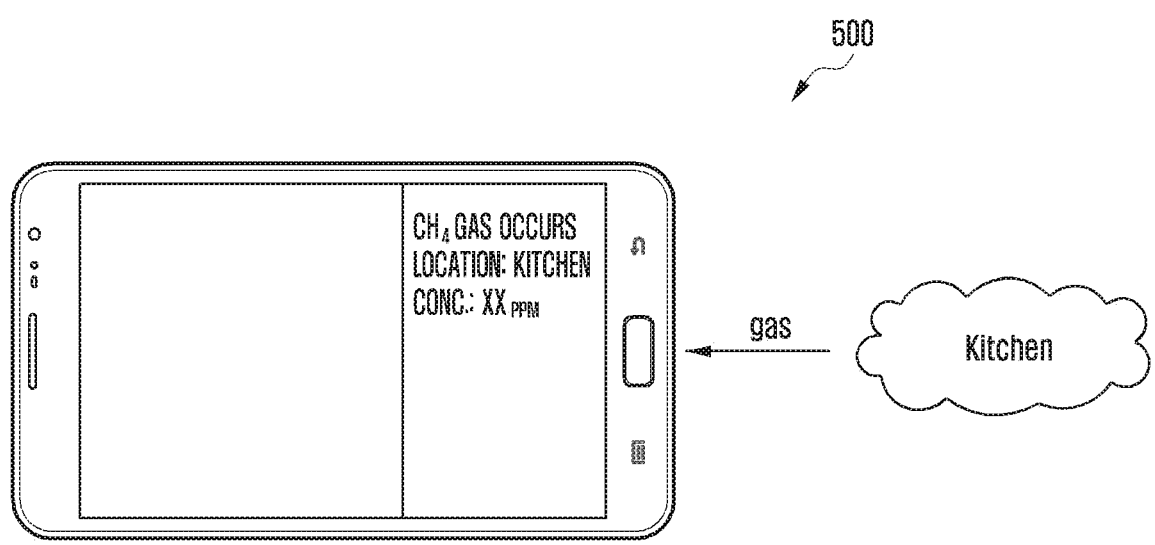
FIGS. 9A and 9B illustrate a user interface for notifying a gas detection according to various embodiments of the present invention.
Figure 9B:
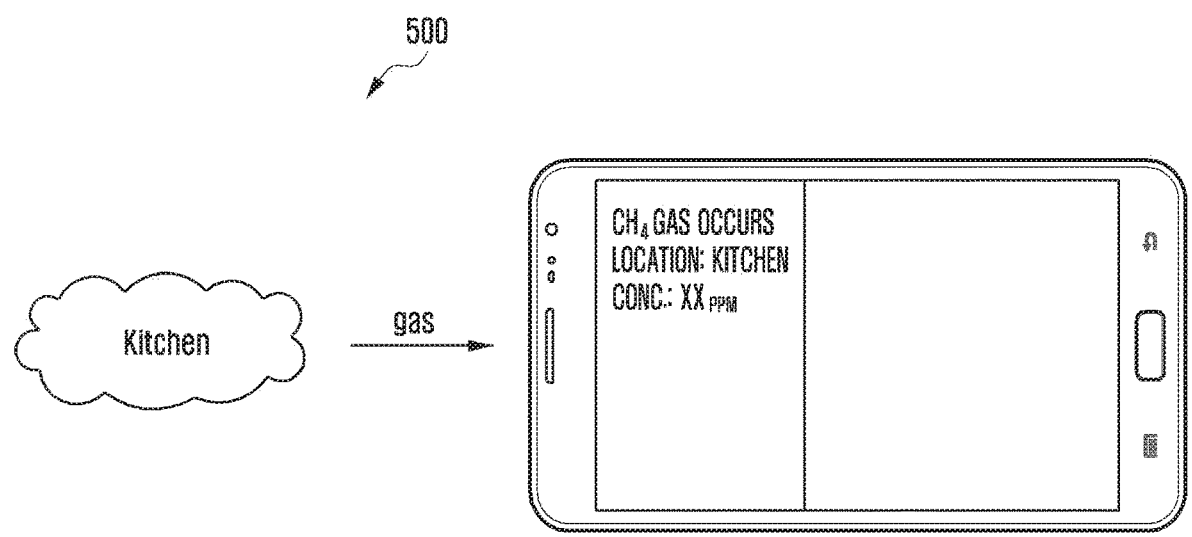

FIGS. 9A and 9B illustrate a user interface for notifying a gas detection according to various embodiments of the present invention.

When any gas occurrence is detected by the first gas sensor 531 and/or the second gas sensor 533, the electronic device 500 may output a warning alarm indicating the detection of gas. The warning alarm may indicate information about an occurring gas type, an occurring location, and a gas concentration. For example, as shown in FIGS. 9A and 9B, the user interface may display on the display 540 that $CH_4$ gas occurs in a kitchen at a concentration of XX ppm.

FIG. 9A shows the user interface displayed when gas occurs in a kitchen and when the lower end of the electronic device 500 faces the kitchen. As shown in FIG. 9A, the second gas sensor 533 located at the lower end of the electronic device 500 may detect the gas occurrence earlier than the first gas sensor 531, so that the processor 510 may recognize that gas occurs in the kitchen located toward lower end of the electronic device 500. In this case, the processor 510 may display a warning message on a lower part of the display 540 so that the user can intuitively know the gas occurrence direction. FIG. 9B shows the user interface displayed when gas occurs in a kitchen and when the upper end of the electronic device 500 faces the kitchen. As shown in FIG. 9B, the first gas sensor 531 located at the upper end of the electronic device 500 may detect the gas occurrence earlier than the second gas sensor 533, so that the processor 510 may recognize that gas occurs in the kitchen located toward the upper end of the electronic device 500. In this case, the processor 510 may display a warning message on an upper part of the display 540 so that the user can intuitively know the gas occurrence direction.

According to various embodiments, the electronic device 500 may provide various emphasized notifications in the gas occurrence direction. For example, the processor 510 may offer the notifications to the user in various manners such as flashing at least a portion of the display 540, displaying a separate icon, or outputting a certain sound through the speaker in the gas occurrence direction.

Figure 10:
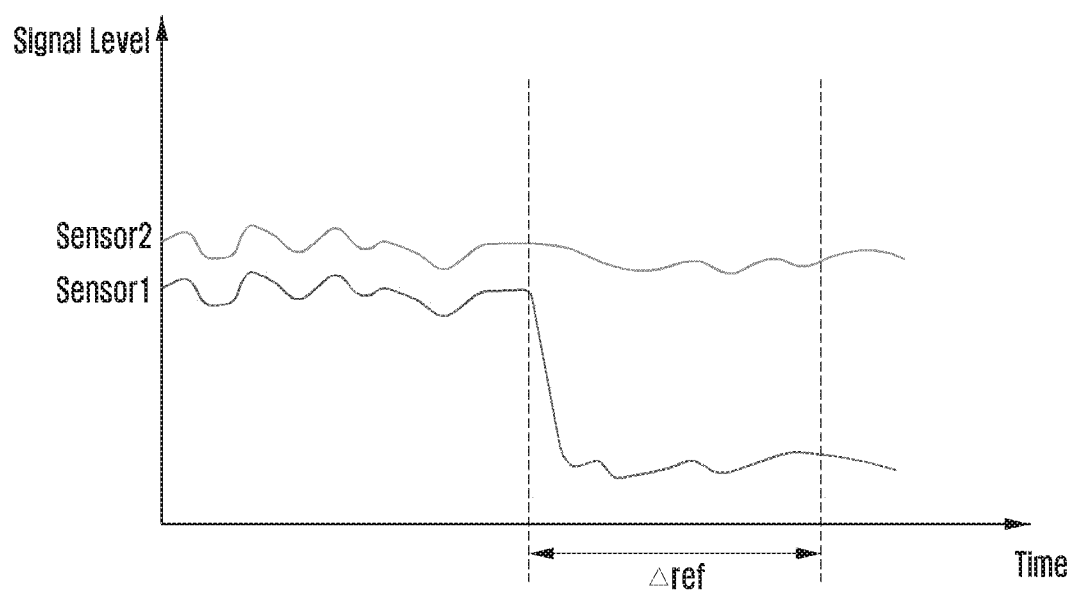
FIG. 10 is a graph showing time-varying signal levels of first data and second data according to various embodiments of the present invention.

FIG. 10 is a graph showing time-varying signal levels of first and second data detected by first and second gas sensors according to various embodiments of the present invention. FIG. 10 shows signal levels detected by the first and/or second gas sensor(s) in a state of malfunction.

When both the first gas sensor 531 and the second gas sensor 533 are equipped in the electronic device 500, a distance between the first and second gas sensors 531 and 533 is not so large due to the size limitation of the electronic device 500. Therefore, considering a gas diffusion speed, a varying time point of the output signal from the first gas sensor 531 and a varying time point of the output signal from the second gas sensor 533 may have a short gap in time.

The first and second gas sensors 531 and 533 of the electronic device 500 may measure the gas in the same measurement place. The output signals of the first and second gas sensors 531 and 533 may have similar output values. Although the output signal variations of the first and second gas sensors 531 and 533 may have a time difference, such signal variations may be similar.

The first and second gas sensors 531 and 533 are semiconductor sensors and may be equipped in the first and second holes, respectively. Therefore, any contaminant may be in contact with the first gas sensor 531 and/or the second gas sensor 533, and this may cause a shift in output value and result in a malfunction of wrongly determining that the gas is detected.

The processor 510 may compare the first data and the second data, and if a difference between two signals is maintained for a specific time, may determine that a malfunction of the gas sensor occurs. For example, when the output signal level of the first gas sensor 531 and/or the second gas sensor 533 is lowered in a gas non-detection area, it may be determined that a malfunction of the gas sensor occurs.

In addition, the processor 510 may compute a difference between a first time point of detecting the gas around the electronic device by using the first gas sensor 531 and a second time point of detecting the gas around the electronic device by using the second gas sensor 533. Then, based on the computed difference in time point, the processor 510 may determine the malfunction of the first gas sensor 531 and/or the second gas sensor 533. That is, when a varying time point of the output signal from the first gas sensor 531 and a varying time point of the output signal from the second gas sensor 533 have a gap equal to or greater than a reference time, it may be determined that a malfunction occurs.

Figure 11:
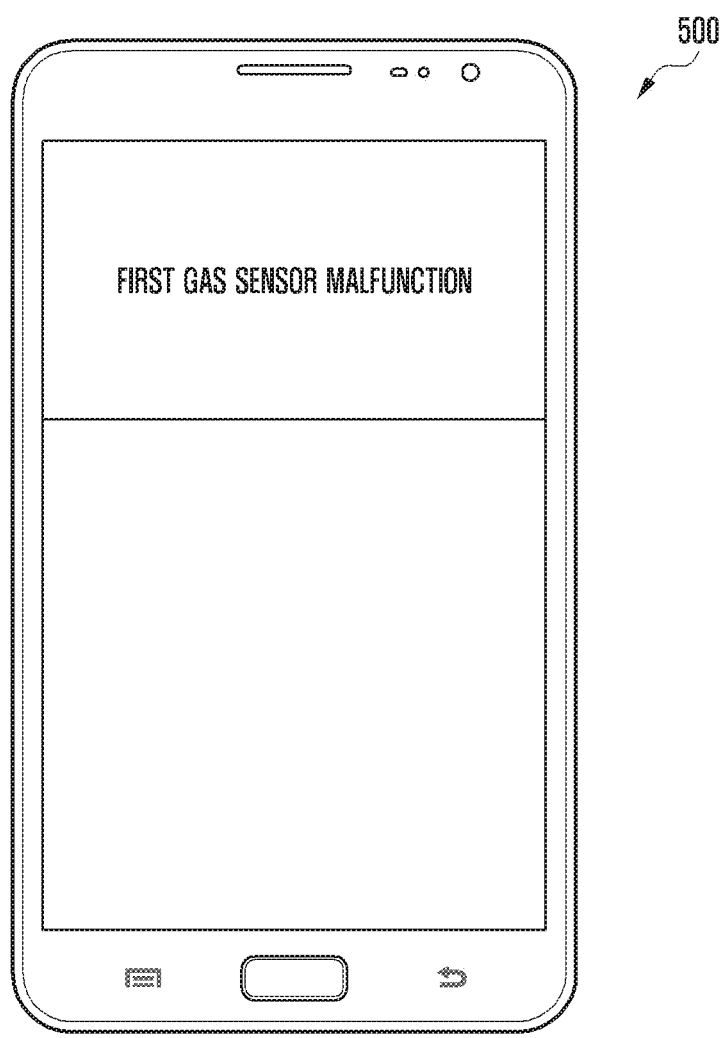
FIG. 11 illustrates a user interface for notifying a malfunction of a gas sensor according to various embodiments of the present invention.

FIG. 11 illustrates a user interface for notifying a malfunction of a gas sensor according to various embodiments of the present invention.

As shown, when it is detected that a malfunction occurs in the first gas sensor 531 and/or the second gas sensor 533, the processor may output the user interface on the display 540. According to various embodiments, the electronic device 500 may provide various notifications when there is a malfunction. For example, the electronic device 500 may offer the notifications to the user in various manners such as flashing at least a portion of the display 540, displaying a separate icon, or outputting a certain sound through the speaker in the gas occurrence direction.

Figure 12:
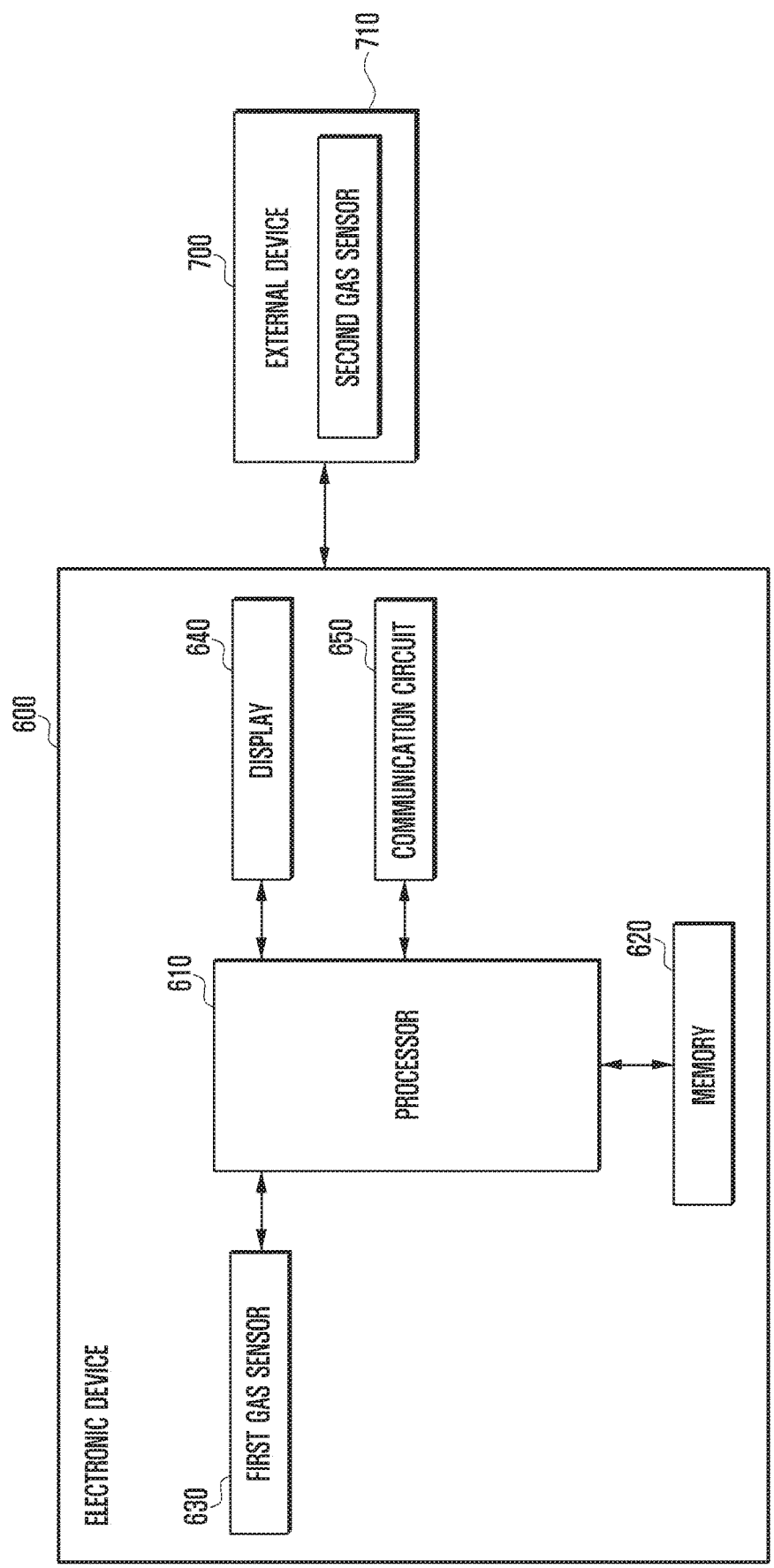
FIG. 12 is a block diagram illustrating an electronic device according to another one of various embodiments of the present invention.

FIG. 12 is a block diagram illustrating an electronic device according to another one of various embodiments of the present invention.

In this embodiment, the electronic device 600 includes a first gas sensor 630, and an external device 700 includes a second gas sensor 710. In addition, using a first data acquired by the first gas sensor 630 and a second data acquired by the second gas sensor 710 of the external device 700, the electronic device 600 provides related information. Hereinafter, description will be made regarding technical features different from embodiments described above with reference to FIGS. 5 to 11, and description of the same technical features will be omitted.

As shown in FIG. 12, the electronic device 600 according to this embodiment may include the first gas sensor 630, a processor 610, a memory 620, a display 640, and a communication circuit 650. Even if at least some of elements shown in FIG. 12 are omitted or substituted, it is possible to implement various embodiments of the present invention.

The external device 700 may be the same kind of device as or a different kind of device from the electronic device 600. Any device that includes a gas sensor and has a wired and/or wireless communication function may be used as the external device 700 according to this embodiment.

The first gas sensor 630 may monitor the gas outside the housing of the electronic device 600 and thereby acquire the first data. The second gas sensor 710 of the external device 700 may monitor the gas outside the external device 700 and thereby acquire the second data. The communication circuit 650 may receive the second data from the external device 700.

The processor 610 may compare the first data and the second data, and based on at least a part of comparison results, may provide information related to a detected gas and/or the first gas sensor 630 and/or the second gas sensor 710 through a user interface.

In this case, the user interface may include the same contents as the user interface described above with reference to FIGS. 5 to 11.

Figure 13:
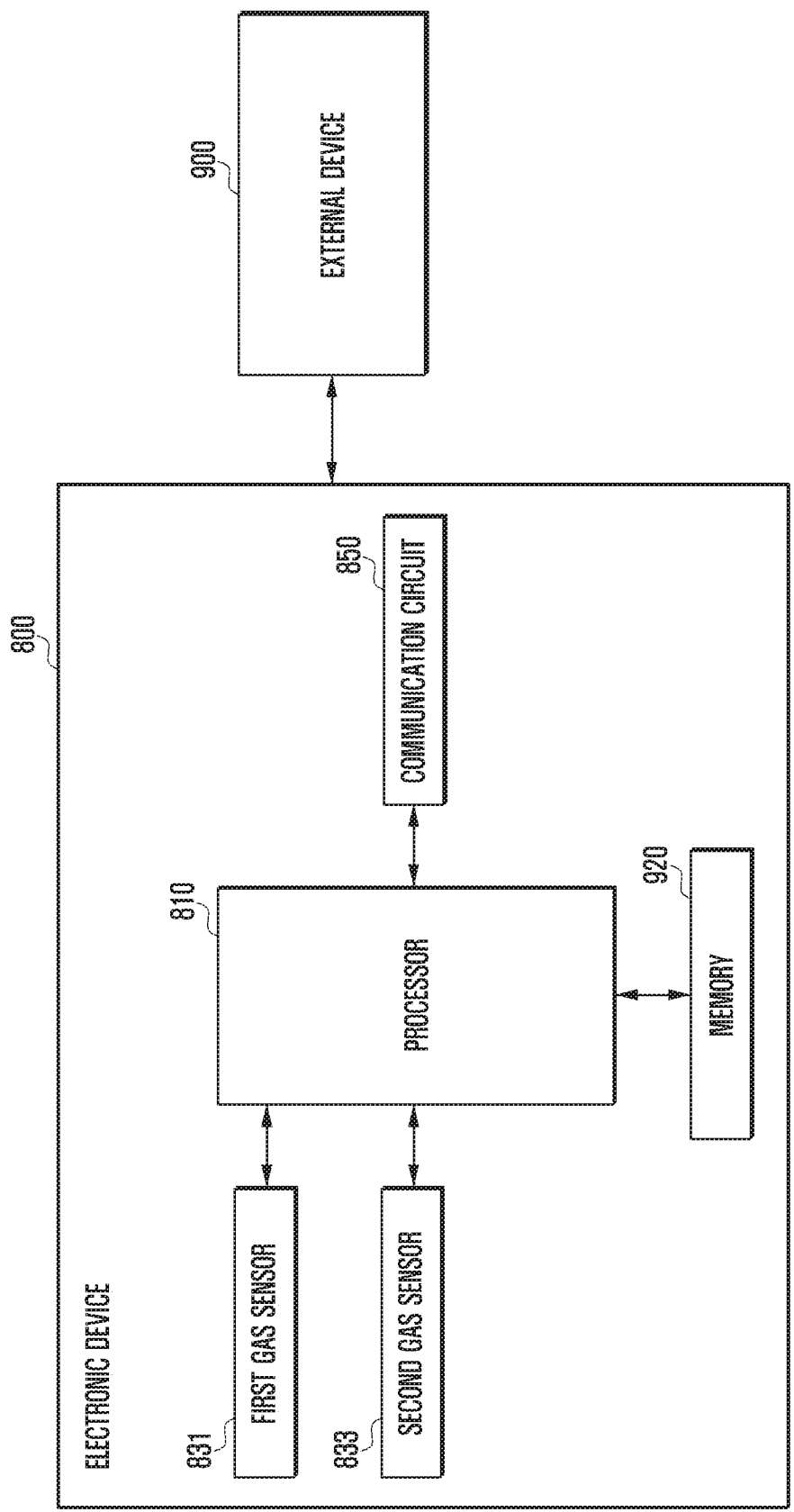
FIG. 13 is a block diagram illustrating an electronic device according to still another one of various embodiments of the present invention.

FIG. 13 is a block diagram illustrating an electronic device according to still another one of various embodiments of the present invention.

In this embodiment, the electronic device 800 includes a first gas sensor 831 and a second gas sensor 833. The electronic device 800 determines a gas occurrence place, based on a first data acquired by the first gas sensor 831 and a second data acquired by the second gas sensor 833, and requests an external device to perform at least one action.

As shown in FIG. 13, the electronic device 800 according to this embodiment may include the first gas sensor 831, the second gas sensor 833, a processor 810, a memory 820, and a communication circuit 850. Even if at least some of elements shown in FIG. 13 are omitted or substituted, it is possible to implement various embodiments of the present invention.

The external device 900 may be the same kind of device as or a different kind of device from the electronic device 800. Any device that has a wired and/or wireless communication function may be used as the external device 900 according to this embodiment.

The first gas sensor 831 may monitor the gas outside the housing of the electronic device 800 and thereby acquire the first data, and the second gas sensor 833 may monitor the gas outside the housing of the electronic device 800 and thereby acquire the second data.

The processor 810 may determine a gas occurrence place, based on the first data and the second data. A method for determining the gas occurrence place may be the same as previously described through FIGS. 8 and 9.

Using the communication circuit 850, the processor 810 may transmit a request for performing at least one action to the external device 900 that is located near the gas occurrence place.

The external device 900 that receives the above request may perform the requested action. This action may be, for example, outputting a GUI or audio signal for notifying the gas occurrence.

An electronic device according to various embodiments of the present invention may comprise a housing; a user interface; a first gas sensor disposed to sense a gas outside the housing; a second gas sensor disposed to sense the gas outside the housing, spaced apart from the first gas sensor, and having a same type as the first gas sensor; a processor electrically connected to the user interface, the first gas sensor, and the second gas sensor; and a memory electrically connected to the processor, wherein the memory stores instructions that cause, upon execution, the processor to acquire a first data while monitoring the gas outside the housing by using the first gas sensor, to acquire a second data while monitoring the gas outside the housing by using the second gas sensor, to compare the first data and the second data, and to provide information related to at least one of the gas, the first gas sensor, or the second gas sensor through the user interface, based on at least a part of comparison results.

According to various embodiments, the instructions may include instructions causing the processor to determine an occurrence direction of the gas or a malfunction of the first or second gas sensor, based on at least a part of the comparison results.

According to various embodiments, the housing may include a first hole formed in a portion of the housing, and a second hole formed in another portion of the housing, the first gas sensor may be disposed in the first hole, and the second gas sensor may be disposed in the second hole.

According to various embodiments, the first hole may be bored into a first surface of the housing in a first direction, and the second hole may be bored into a second surface of the housing in a second direction opposite to the first direction.

According to various embodiments, the electronic device may further comprise at least one of at least one microphone and at least one speaker, and the at least one of the at least one microphone and the at least one speaker may be configured to acquire or output a sound signal through the first hole or the second hole.

According to various embodiments, the electronic device may further comprise at least one another sensor, and the instructions may cause the processor to determine an occurrence direction of the gas or a malfunction of the first or second gas sensor, further based on a third data monitored using the at least one another sensor. This sensor may include various types of sensors such as an orientation sensor, a velocity sensor, a temperature sensor, a humidity sensor, and the like. In case of the gas sensor, an electric signal output may be partially changed depending on temperature and humidity at the same concentration. Therefore, the first data and the second data may have different values depending on ambient environments such as temperature and humidity. The electronic device may store a compensation table that compensates for the values of the first and second data outputted from the gas sensor, based on the temperature and humidity values. When the first and second data are detected by the first and second gas sensors, the electronic device may compensate for the values of the first and second data by using the compensation table on the basis of the temperature and humidity values included in the third data.

According to various embodiments, the instructions may cause the processor to determine a difference between a first time point of detecting the gas around the electronic device by using the first gas sensor and a second time point of detecting the gas around the electronic device by using the second gas sensor.

According to various embodiments, the instructions may cause the processor to determine an occurrence direction of the gas or a malfunction of the first or second gas sensor, based on the determined difference in time point.

In addition, an electronic device according to various embodiments may comprise a housing; a user interface; a communication circuit disposed in the housing; a first gas sensor disposed to sense a gas outside the housing; a processor electrically connected to the communication circuit, the user interface, and the first gas sensor; and a memory electrically connected to the processor, wherein the memory stores instructions that cause, upon execution, the processor to acquire a first data while monitoring the gas outside the housing by using the first gas sensor, to acquire a second data associated with a gas, monitored through a second gas sensor included in an external device, around the external device from the external device by using the communication circuit, to compare the first data and the second data, and to provide information related to at least one of the gas outside the housing, the gas around the external device, the first gas sensor, or the second gas sensor through the user interface, based on at least a part of comparison results.

In addition, an electronic device according to various embodiments may comprise a housing; a communication circuit disposed in the housing; first and second gas sensors disposed to sense a gas outside the housing; a processor electrically connected to the first and second gas sensors; and a memory electrically connected to the processor, wherein the memory stores instructions that cause, upon execution, the processor to acquire a first data while monitoring the gas outside the housing by using the first gas sensor, to acquire a second data while monitoring the gas outside the housing by using the second gas sensor, to determine a gas occurrence place, based on the first and second data, and to transmit to an external device located near the gas occurrence place, by using the communication circuit, a request for the external device to perform at least one action.

Figure 14:
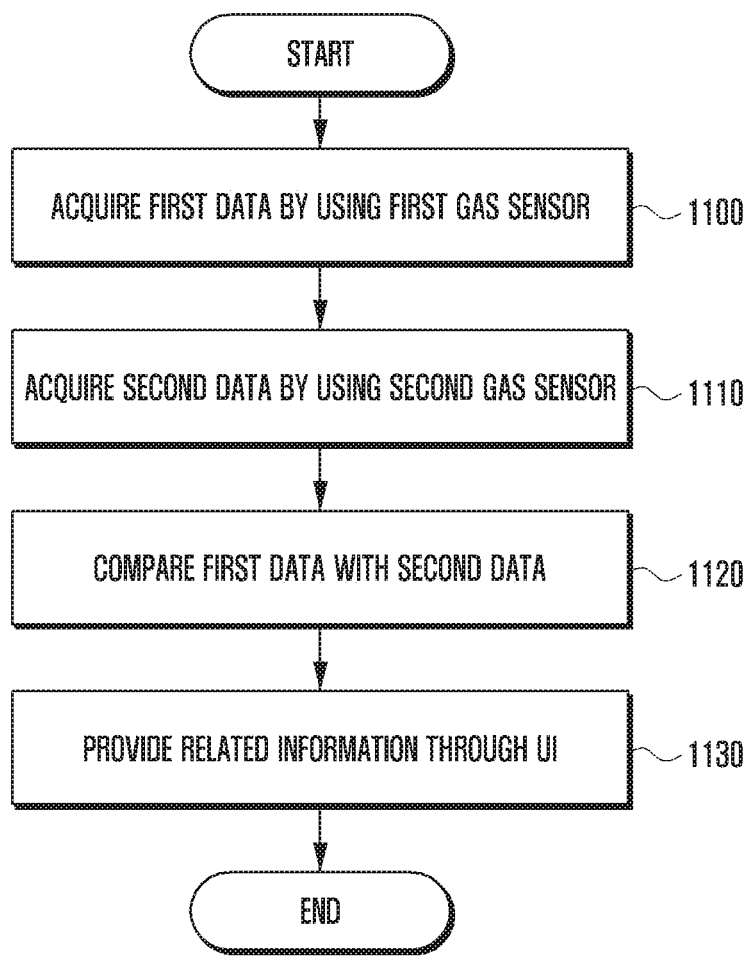
FIG. 14 is a flow diagram illustrating a method for utilizing a gas sensor according to various embodiments of the present invention.

FIG. 14 is a flow diagram illustrating a method for utilizing a gas sensor according to various embodiments of the present invention.

The illustrated method may be implemented by the electronic device according to various embodiments described above with reference to FIGS. 1 to 13, and the description of technical features already described will be omitted below.

At operation 1100, the electronic device acquires the first data by using the first gas sensor.

At operation 1110, the electronic device acquires the second data by using the second gas sensor.

The operations 1100 and 1110 may be performed simultaneously, and their order may change.

At operation 1120, the electronic device compares the acquired first and second data.

At operation 1130, the electronic device may provide information related to the gas and the first and/or second gas sensor(s) via the user interface, based on at least a part of results of the comparison at operation 1120. Here, the information provided through the user interface may include a warning alarm indicating the detection of gas. The warning alarm may indicate information about an occurring gas type, an occurring location, and a gas concentration.

Figure 15:
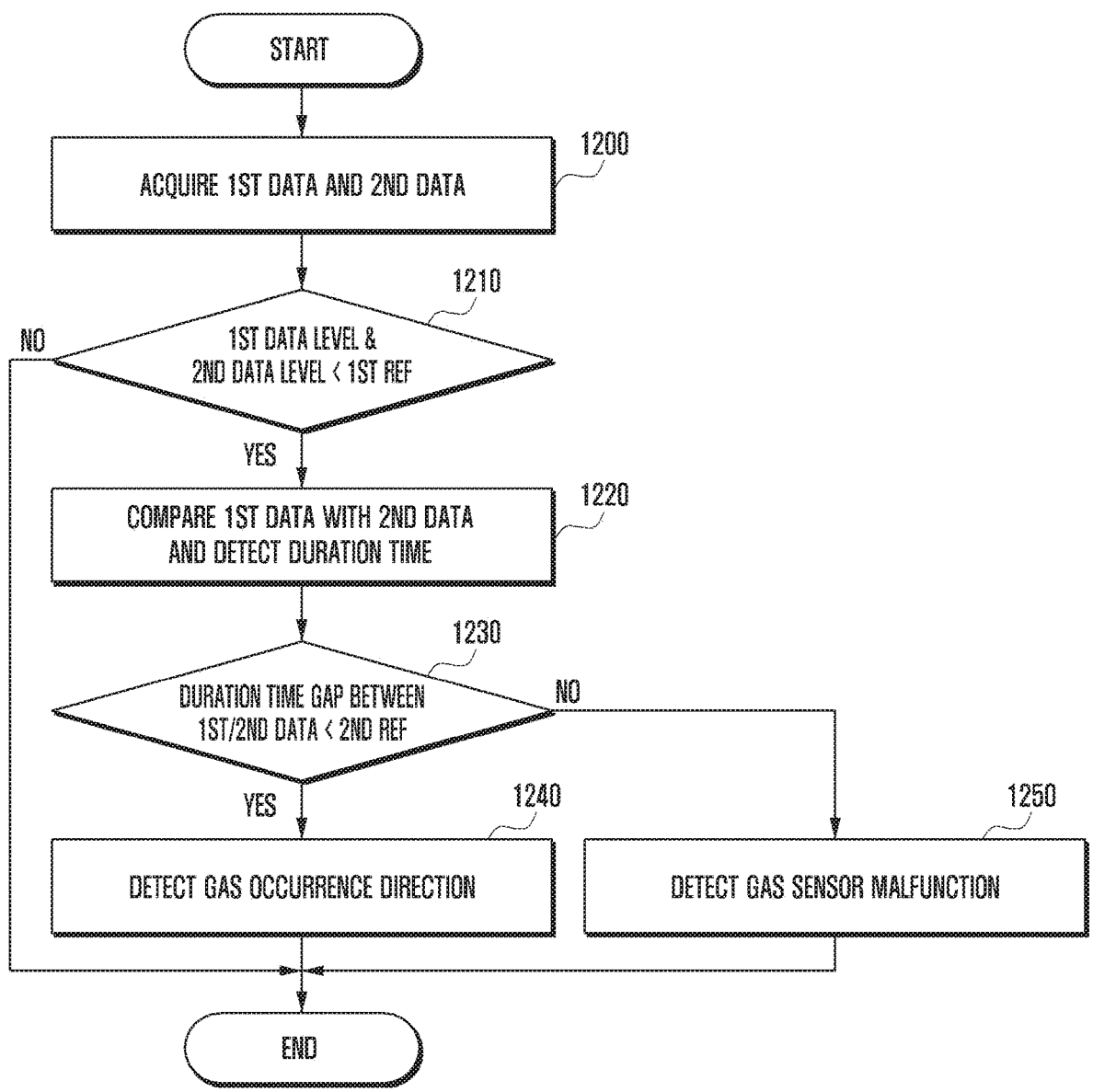
FIG. 15 is a flow diagram illustrating a process of detecting a gas occurrence direction or a gas sensor malfunction in a utilization method of a gas sensor according to various embodiments of the present invention.

FIG. 15 is a flow diagram illustrating a process of detecting a gas occurrence direction or a gas sensor malfunction in a utilization method of a gas sensor according to various embodiments of the present invention.

The illustrated method may be implemented by the electronic device according to various embodiments described above with reference to FIGS. 1 to 13, and the description of technical features already described will be omitted below.

At operation 1200, the electronic device acquires the first data and the second data.

At operation 1210, the electronic device determines whether the level of the first data acquired through the first gas sensor is lower than the first reference value and whether the level of the second data acquired through the second gas sensor is lower than the first reference value. As described above, the gas sensor may change its electrical property when the gas is detected. Therefore, when the output level becomes lower than the first reference value, the electronic device may determine that the gas occurs around the electronic device.

At operation 1220, when the level of the first and second data is lower than the first reference value, the electronic device compares the first data and the second data and detects a duration time of the output level of the first and second data.

At operation 1230, the electronic device determines whether a duration time gap between the first data and the second data is smaller than the second reference value.

At operation 1240, if the duration time gap is smaller than the second reference value, the electronic device determines that the first and second gas sensors detect the gas while operating normally, and then detects a gas occurrence direction. Here, the gas occurrence direction may be determined as a direction in which the gas sensor detecting a signal whose output level is lowered earlier is located. In this case, information related to the gas and the first and/or second gas sensor(s) may be provided through the user interface.

At operation 1250, if the duration time gap is not smaller than the second reference value, the electronic device may determine that a malfunction occurs in the first and/or second gas sensor(s). In this case, it is possible to provide a user interface indicating whether the gas sensor malfunctions.

Figure 16:
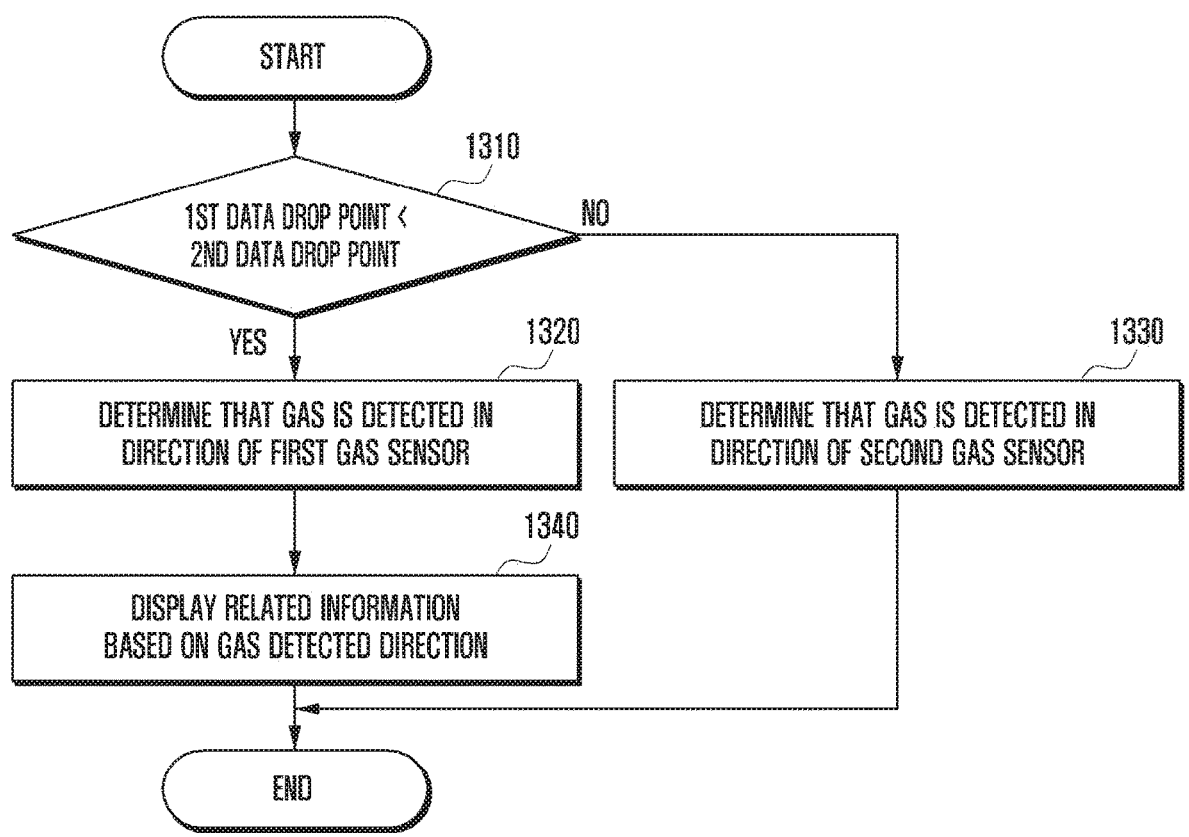
FIG. 16 is a flow diagram illustrating a process of detecting a gas occurrence direction in a utilization method of a gas sensor according to various embodiments of the present invention.

FIG. 16 is a flow diagram illustrating a process of detecting a gas occurrence direction in a utilization method of a gas sensor according to various embodiments of the present invention.

The illustrated method may be implemented by the electronic device according to various embodiments described above with reference to FIGS. 1 to 13, and the description of technical features already described will be omitted below.

At operation 1310, the electronic device compares a varying time point of the first data and a varying time point of the second data. Here, the varying time point may mean a drop point, i.e., a time point at which the output level of the first and second data falls below a predetermined reference value.

At operation 1320, if the drop point of the first data is earlier than that of the second data, the electronic device may determine that the gas is detected in the direction where the first gas sensor is located.

At operation 1330, if the drop point of the second data is earlier than that of the first data, the electronic device may determine that the gas is detected in the direction where the second gas sensor is located.

At operation 1340, the electronic device may provide the display with related information such as a warning alarm to indicate the gas detection, and information about an occurring gas type, an occurring location, and a gas concentration, depending on a gas detection direction.

A method for utilizing a gas sensor according to various embodiments of the present invention may comprise acquiring a first data while monitoring a gas outside an electronic device by using a first gas sensor; acquiring a second data while monitoring the gas outside the electronic device by using a second gas sensor spaced apart from the first gas sensor and having a same type as the first gas sensor; comparing the first data and the second data; and providing information related to at least one of the gas, the first gas sensor, or the second gas sensor through a user interface, based on at least a part of comparison results.

According to various embodiments, the comparing the first data and the second data may include determining an occurrence direction of the gas or a malfunction of the first or second gas sensor, based on at least a part of the comparison results.

According to various embodiments, the method may further comprise acquiring a third data by using at least one another sensor included in the electronic device, and the comparing the first data and the second data may include determining an occurrence direction of the gas or a malfunction of the first or second gas sensor, further based on the third data. This sensor may include various types of sensors such as an orientation sensor, a velocity sensor, a temperature sensor, a humidity sensor, and the like. In case of the gas sensor, an electric signal output may be partially changed depending on temperature and humidity at the same concentration. Therefore, the first data and the second data may have different values depending on ambient environments such as temperature and humidity. The electronic device may store a compensation table that compensates for the values of the first and second data outputted from the gas sensor, based on the temperature and humidity values. When the first and second data are detected by the first and second gas sensors, the electronic device may compensate for the values of the first and second data by using the compensation table on the basis of the temperature and humidity values included in the third data.

According to various embodiments, the comparing the first data and the second data may include determining a difference between a first time point of detecting the gas around the electronic device by using the first gas sensor and a second time point of detecting the gas around the electronic device by using the second gas sensor.

According to various embodiments, the comparing the first data and the second data may include determining an occurrence direction of the gas or a malfunction of the first or second gas sensor, based on the determined difference in time point.

A method for utilizing a gas sensor according to various embodiments of the present invention may comprise acquiring a first data while monitoring a gas outside an electronic device by using a first gas sensor; receiving, from an external device, a second data associated with a gas around the external device and acquired using a second gas sensor included in the external device and having a same type as the first gas sensor; comparing the first data and the second data; and providing information related to at least one of the gas, the first gas sensor, or the second gas sensor through a user interface, based on at least a part of comparison results.

A method for utilizing a gas sensor according to various embodiments of the present invention may comprise acquiring a first data while monitoring the gas outside the housing by using the first gas sensor; acquiring a second data while monitoring the gas outside the housing by using the second gas sensor; determining a gas occurrence place, based on the first and second data; and transmitting to an external device located near the gas occurrence place, by using the communication circuit, a request for the external device to perform at least one action.

What is claimed is:

1. An electronic device comprising:
   a housing;
   a first gas sensor configured to sense a gas outside the housing;
   a second gas sensor configured to sense the gas outside the housing, spaced apart from the first gas sensor, and having a same type as the first gas sensor;
   a processor operatively connected to the first gas sensor and the second gas sensor; and
   a memory electrically connected to the processor,
   wherein the memory stores instructions that cause, upon execution, the processor to:
      acquire a first data while monitoring the gas outside the housing by using the first gas sensor,
      acquire a second data while monitoring the gas outside the housing by using the second gas sensor,
      compare the first data and the second data,
      determine an occurrence direction of the gas relative to the electronic device based on comparison results of the first data and the second data, and
      provide a user interface by at least one of a display or a speaker including information related to the occurrence direction of the gas relative to the electronic device, based on the determination, and
   wherein a location of the first gas sensor on the housing of the electronic device is opposite that of the location of the second gas sensor on the housing of the electronic device.

2. The electronic device of claim 1, wherein the instructions include instructions causing the processor to determine a malfunction of the first or second gas sensor, based on at least a part of the comparison results.

3. The electronic device of claim 1,
   wherein the housing includes a first hole formed in a portion of the housing, and a second hole formed in another portion of the housing,
   wherein the first gas sensor is disposed in the first hole, and
   wherein the second gas sensor is disposed in the second hole.

4. The electronic device of claim 3,
   wherein the first hole is bored into a first surface of the housing in a first direction, and
   wherein the second hole is bored into a second surface of the housing in a second direction opposite to the first direction.

5. The electronic device of claim 3, further comprising:
   at least one of at least one microphone and at least one speaker,
   wherein the at least one of the at least one microphone and the at least one speaker is configured to acquire or output a sound signal through the first hole or the second hole.

6. The electronic device of claim 1, further comprising:
   at least one another sensor,
   wherein the instructions cause the processor to determine the occurrence direction of the gas, further based on a third data monitored using the at least one another sensor.

7. The electronic device of claim 1, wherein the instructions cause the processor to determine a difference between a first time point of detecting the gas around the electronic device by using the first gas sensor and a second time point of detecting the gas around the electronic device by using the second gas sensor.

8. The electronic device of claim 7, wherein the instructions cause the processor to determine the occurrence direction of the gas, based on the determined difference in time point.

9. An electronic device comprising:
   a housing;
   a communication circuit disposed in the housing;
   a first gas sensor configured to sense a gas outside the housing;
   a processor electrically connected to the communication circuit, and the first gas sensor; and
   a memory operatively connected to the processor,
   wherein the memory stores instructions that cause, upon execution, the processor to:
      acquire a first data while monitoring the gas outside the housing by using the first gas sensor,
      acquire a second data associated with a gas, monitored through a second gas sensor included in an external device, around the external device from the external device by using the communication circuit,
      compare the first data and the second data,
      determine an occurrence direction of the gas relative to the electronic device based on comparison results of the first data and the second data, and
      provide a user interface by at least one of a display or a speaker including information related to the occurrence direction of the gas relative to the electronic device, based on the determination, and
   wherein a location of the first gas sensor on the housing of the electronic device is opposite that of the location of the second gas sensor on the housing of the electronic device.

10. A method comprising:
    acquiring a first data while monitoring a gas outside an electronic device by using a first gas sensor;

acquiring a second data while monitoring the gas outside the electronic device by using a second gas sensor spaced apart from the first gas sensor and having a same type as the first gas sensor;

comparing the first data and the second data;

determining an occurrence direction of the gas relative to the electronic device based on comparison results of the first data and the second data; and providing a user interface including information related to the occurrence direction of the gas relative to the electronic device, based on the determination, wherein a location of the first gas sensor on a housing of the electronic device is opposite that of the location of the second gas sensor on the housing of the electronic device.

11. The method of claim 10, wherein the comparing the first data and the second data includes determining a malfunction of the first or second gas sensor, based on at least a part of the comparison results.

12. The method of claim 10, further comprising:

acquiring a third data by using at least one another sensor included in the electronic device, wherein the comparing the first data and the second data includes determining the occurrence direction of the gas, further based on the third data.

13. The method of claim 10, wherein the comparing the first data and the second data includes determining a difference between a first time point of detecting the gas around the electronic device by using the first gas sensor and a second time point of detecting the gas around the electronic device by using the second gas sensor.

14. The method of claim 13, wherein the comparing the first data and the second data includes determining the occurrence direction of the gas, based on the determined difference in time point.

15. A method comprising:

acquiring a first data while monitoring a gas outside an electronic device by using a first gas sensor;

receiving, from an external device, a second data associated with a gas around the external device and acquired using a second gas sensor included in the external device and having a same type as the first gas sensor;

comparing the first data and the second data;

determining an occurrence direction of the gas relative to the electronic device based on comparison results of the first data and the second data; and providing a user interface including information related to the occurrence direction of the gas relative to the electronic device, based on the determination, wherein a location of the first gas sensor on a housing of the electronic device is opposite that of the location of the second gas sensor on the housing of the electronic device.

* * * * *